US010209232B2

(12) United States Patent
Forzani et al.

(10) Patent No.: US 10,209,232 B2
(45) Date of Patent: Feb. 19, 2019

(54) SPECIFIC, REVERSIBLE, AND WIDE-DYNAMIC RANGE SENSOR FOR REAL TIME DETECTION OF CARBON DIOXIDE

(71) Applicant: Arizona Board of Regents on behalf of Arizona State University, Scottsdale, AZ (US)

(72) Inventors: Erica Forzani, Mesa, AZ (US); Nongjian Tao, Fountain Hills, AZ (US); Di Zhao, Tempe, AZ (US); Francis Tsow, Tempe, AZ (US)

(73) Assignee: ARIZONA BOARD OF REGENTS ON BEHALF OF ARIZONA STATE UNIVERSITY, Scottsdale, AZ (US)

( * ) Notice: Subject to any disclaimer, the term of this patent is extended or adjusted under 35 U.S.C. 154(b) by 44 days.

(21) Appl. No.: 15/104,668

(22) PCT Filed: Dec. 17, 2014

(86) PCT No.: PCT/US2014/070809
§ 371 (c)(1),
(2) Date: Jun. 15, 2016

(87) PCT Pub. No.: WO2015/102902
PCT Pub. Date: Jul. 9, 2015

(65) Prior Publication Data
US 2016/0313290 A1    Oct. 27, 2016

Related U.S. Application Data

(60) Provisional application No. 61/923,048, filed on Jan. 2, 2014.

(51) Int. Cl.
*G01N 1/22* (2006.01)
*G01N 31/00* (2006.01)
(Continued)

(52) U.S. Cl.
CPC ........ *G01N 33/004* (2013.01); *A61B 5/0022* (2013.01); *A61B 5/0059* (2013.01);
(Continued)

(58) Field of Classification Search
CPC ........... G01N 1/22; G01N 31/00; G01N 33/00
(Continued)

(56) References Cited

U.S. PATENT DOCUMENTS

| 4,943,364 A | 7/1990 | Koch et al. |
| 4,994,117 A | 2/1991 | Fehder |

(Continued)

OTHER PUBLICATIONS

Zhao et al., A personal device for analyzing carbon dioxide in real time and real breath: Experimental investigation and computational simulation., Sensors and Actuators B: Chemical, Jul. 2013, 183:627-35.

(Continued)

*Primary Examiner* — Brian J. Sines
(74) *Attorney, Agent, or Firm* — George A. Leone; Citadel Patent Law

(57) ABSTRACT

A $CO_2$ detection chamber includes a gas inlet and a gas outlet. A $CO_2$ sensor is housed in the $CO_2$ detection chamber, where the sensor includes a reversible and selective pH-sensitive nanocomposite sensor element for $CO_2$ detection, and a hydrophobic surface. A flowmeter, a thermistor and a humidity sensor operate to read flow and compensate for humidity conditions. A light source is coupled to receive signals from the $CO_2$ sensor and respond to color changes in the sensor by transducing the color change into a light intensity change. A photodiode receives signals from the light source and responds to light intensity changes by transducing the light intensity changes into electronic sig- (Continued)

nals representing varying degrees of light intensity. Data representing $CO_2$ measurements is transmitted for display to a mobile device.

11 Claims, 18 Drawing Sheets

(51) Int. Cl.
```
G01N 33/00      (2006.01)
A61B 5/08       (2006.01)
G01N 21/84      (2006.01)
G01N 33/497     (2006.01)
A61B 5/00       (2006.01)
```

(52) U.S. Cl.
CPC .......... *A61B 5/082* (2013.01); *G01N 21/8483* (2013.01); *G01N 33/497* (2013.01); *A61B 2560/0242* (2013.01); *A61B 2560/0252* (2013.01)

(58) Field of Classification Search
USPC .......... 422/83, 84, 85, 98; 436/43, 145, 164, 436/167
See application file for complete search history.

(56) References Cited

U.S. PATENT DOCUMENTS

| | | | |
|---|---|---|---|
| 5,005,572 A | 4/1991 | Raemer et al. | |
| 5,156,159 A | 10/1992 | Lampotang et al. | |
| 6,436,347 B1 | 8/2002 | Cedeon | |
| 6,468,222 B1* | 10/2002 | Mault | A61B 5/0833 600/529 |
| 6,709,403 B1 | 3/2004 | Ratner | |
| 7,578,971 B2 | 8/2009 | Ratner et al. | |
| 8,186,351 B2* | 5/2012 | Munro | A61M 16/04 128/207.14 |
| 8,449,834 B2 | 5/2013 | Ostrowski | |
| 9,347,932 B2 | 5/2016 | Tao et al. | |
| 2007/0048181 A1 | 3/2007 | Chang et al. | |
| 2008/0072905 A1 | 3/2008 | Baker et al. | |
| 2008/0078394 A1 | 4/2008 | Ostrowski | |
| 2009/0095290 A1 | 4/2009 | Cain et al. | |
| 2010/0166604 A1 | 7/2010 | Lim et al. | |
| 2010/0170323 A1 | 7/2010 | Lighton | |
| 2011/0056846 A1* | 3/2011 | Neethirajan | G01N 27/304 205/785.5 |
| 2011/0066061 A1 | 3/2011 | Colman et al. | |
| 2011/0098592 A1* | 4/2011 | Colman | A61M 16/04 600/532 |
| 2012/0330161 A1 | 12/2012 | Kobayashi et al. | |
| 2013/0075794 A1* | 3/2013 | Bradley | B82Y 10/00 257/253 |
| 2013/0150746 A1 | 6/2013 | Tao | |
| 2013/0259749 A1 | 10/2013 | Moretti et al. | |
| 2013/0323845 A1 | 12/2013 | Kane | |
| 2015/0369795 A1 | 12/2015 | Tsow et al. | |

OTHER PUBLICATIONS

Zhao et al., A pocket-sized metabolic analyzer for assessment of resting energy expenditure., Clinical Nutrition, Apr. 2014, 33(2):341-7.
Chuang et al., Using Statistical Techniques to Predict Dynamic Arterial PCO2 in Patients With COPD During Maximum Exercise., Respiratory Care, Jul. 2012, 57(7):1106-14.
Ito et al., Non-invasive prospective targeting of arterial PCO2 in subjects at rest., The Journal of Physiology, Aug. 2008, 586(15):3675-82.
Singh and Singhal, Dose end-tidal carbon dioxide measurement correlate with arterial carbon dioxide in extremely low birth weight infants in the first week of life?., Indian Pediatrics, Jan. 2006, 43(1):20-5.
Richardson, New trends in capnography., Focus on Technology, Nov./Dec. 2008, 42-4.
Gooneratne et al., Chronic Obstructive Pulmonary Disease Diagnosis and Management in Older Adults., Journal of the American Geriatrics Society, Jun. 2010, 58(6):1153-62.
Asaba, Asthma cases increase sixfold in 30 years in Japan, Medical News Today, Sep. 2004, <http://www.medicalnewstoday.com/releases/14222.php>.
Mannino et al., Chronic Obstructive Pulmonary Disease Surveillance—United States, 1971-2000., Morbidity and Mortality Weekly Report, Centers for Disease Control and Prevention, Aug. 2002, 51(SS-6):1-20.
Srinivasa and Kodali, Capnography in "Outside of Hospital Settings"—911., Capnography: A Comprehensive Educational Website, accessed Aug. 19, 2016, 7 pages, <http://www.capnography.com/outside/911.htm>.
Raheem and Wahba, A nasal catheter for the measurement of end-tidal carbon dioxide in spontaneously breathing patients: a preliminary evaluation., Anesthesia and Analgesia, Apr. 2010, 110(4):1039-42.
Kurt et al., The diagnostic role of capnography in pulmonary embolism., The American Journal of Emergency Medicine, May 2010, 28(4):460-5.
Cacho et al., Capnography is superior to pulse oximetry for the detection of respiratory depression during colonoscopy., Revista Espanola de Enfermedades Digestivas, 2010, 102(3):86-9.
Ab-Rahman and Howe, A Comparison of Capnographic Waveform Indices and Peak Flow Meter in the Monitoring of Asthmatic Patients in Emergency Departments., Annals of Emergency Medicine, Apr. 2008, 51(4):476-7.
Yanagidate and Dohi, Modified nasal cannula for simultaneous oxygen delivery and end-tidal CO2 monitoring during spontaneous breathing., European Journal of Anaesthesiology, Mar. 2006, 23(3):257-60.
Persily, The relationship between indoor air quality and carbon dioxide., Indoor Air 1996, The 7th International Conference on Indoor Air Quality and Climate, Jul. 21-26, 1996 (Nagoya, Japan), 2:961-6.
Satish et al., Is CO2 an indoor pollutant? Direct effects of low-to-moderate CO2 concentrations on human decision-making performance., Environmental Health Perspectives, Dec. 2012, 120(12)1671-7.
Erdmann et al., Indoor carbon dioxide concentrations and SBS symptoms in office buildings revisited: Analyses of the 100 building BASE Study dataset., Indoor Air 2002, Proceedings of the Indoor Air 2020 Conference, 2002 (Santa Cruz, CA), 3:443-8.
Soleimanpour et al., Predictive value of capnography for suspected diabetic ketoacidosis in the emergency department, Western Journal of Emergency Medicine, 2013, 14(6):590-4.
Gilhorta and Porter, Predicting diabetic ketoacidosis in children by measuring end-tidal CO2 via non-invasive nasal capnography., Journal of Paediatrics & Child Health, Oct. 2007, 43(10):677-80.
Garcia et al., Capnometry for noninvasive continuous monitoring of metabolic status in pediatric diabetic ketoacidosis., Critical Care Medicine, Oct. 2003, 31(10):2539-43.
Fearon and Steele, End-tidal carbon dioxide predicts the presence and severity of acidosis in children with diabetes., Academic Emergency Medicine, Dec. 2002, 9(12):1373-8.
Kodali, Physical Method of CO2 Measurement., Capnography: A Comprehensive Educational Website, accessed Aug. 22, 2016, 6 pages, <http://www.capnography.com/new/physical-methods-of-co2-measurement>.
Nakamura and Amao, Optical sensor for carbon dioxide combining colorimetric change of a pH indicator and a reference luminescent dye., Analytical and Bioanalytical Chemistry, Jul. 2003, 376(5):642-6.
Segawa et al., Sensitivity of fiber-optic carbon dioxide sensors utilizing indicator dye., Sensors & Actuators: B. Chemical, Oct. 2003, 94(3):276-81.
Borisov et al., Optical carbon dioxide sensors based on silicone-encapsulated room-temperature ionic liquids., Chemistry of Materials, Dec. 2007, 19(25):6187-94.

(56) References Cited

OTHER PUBLICATIONS

Fernandez-Sanchez et al., Optical CO2-sensing layers for clinical application based on pH-sensitive indicators incorporated into nanoscopic metal-oxide supports., Sensors & Actuators: B. Chemical, Dec. 2007, 128(1):145-53.
Carvajal et al., Hand-held optical instrument for CO2 in gas phase based on sensing film coating optoelectronic elements., Sensors & Actuators: B. Chemical, Jan. 2010, 144(1):232-38.
Mills et al., Breath-by-breath measurement of carbon dioxide using a plastic film optical sensor., Sensors & Actuators: B. Chemical, 1997, 39(1):419-25.
Zhao et al., A personal device for analyzing carbon dioxide in real time and real breath: Experimental investigation and computational simulation., Sensors & Actuators: B. Chemical, 2013, 183:627-35.
PCT/2014/070809, Search Report, and Written Opinion of the International Searching Authority, dated Jul. 24, 2015.
PCT/2014/070809, International Preliminary Report on Patentability, dated Jul. 5, 2016.

\* cited by examiner

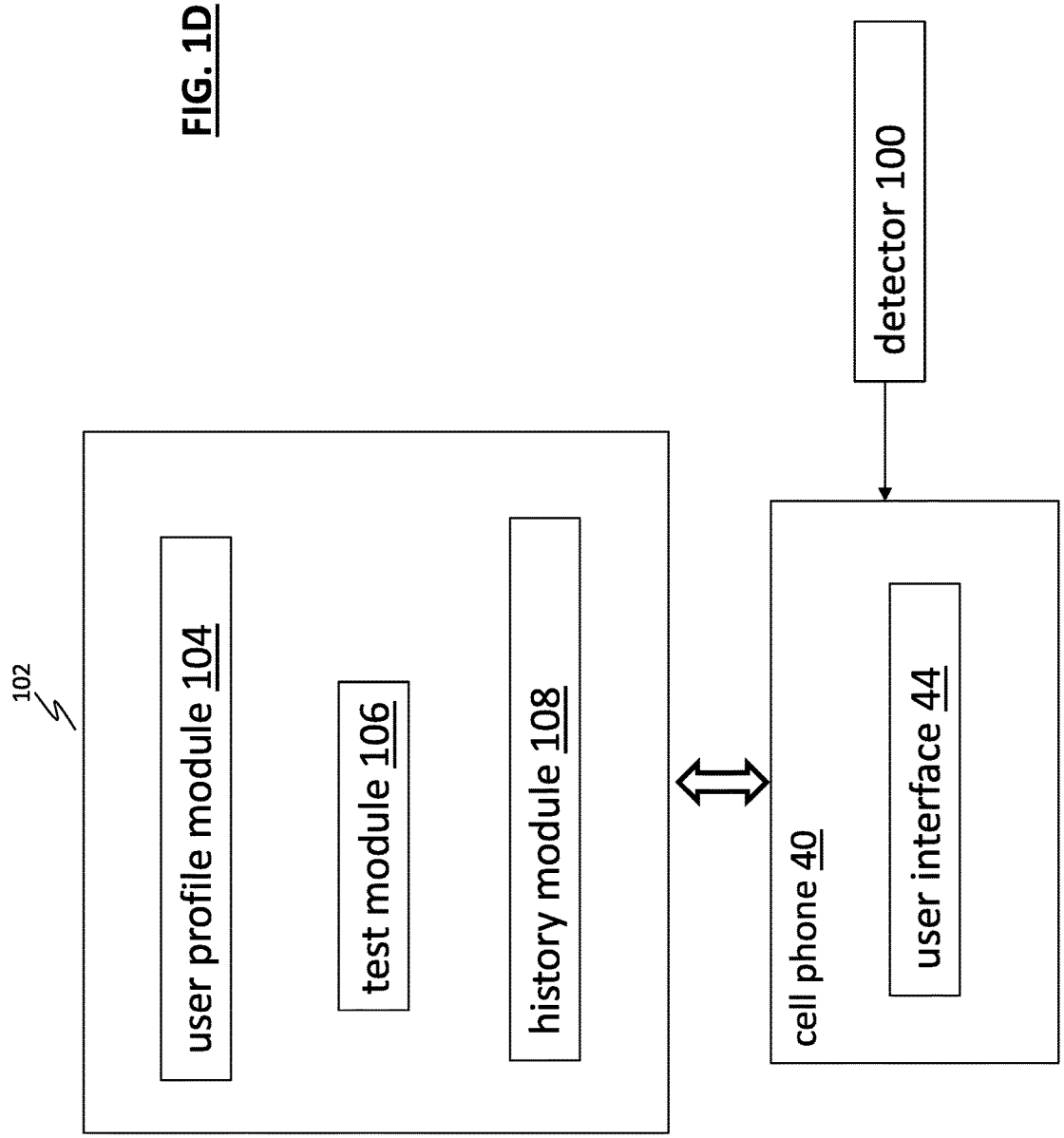

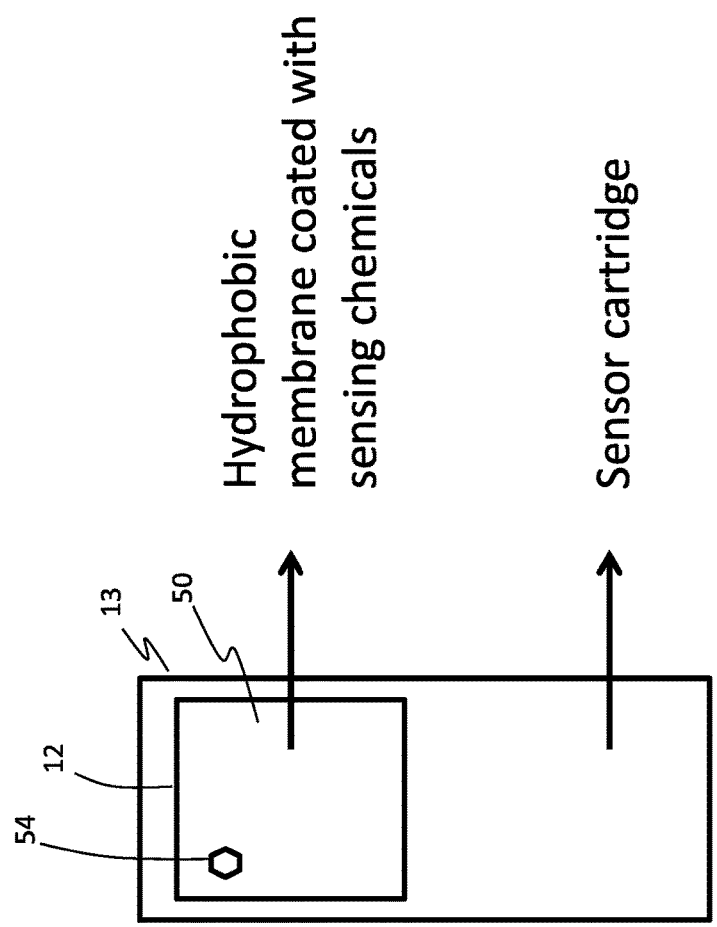

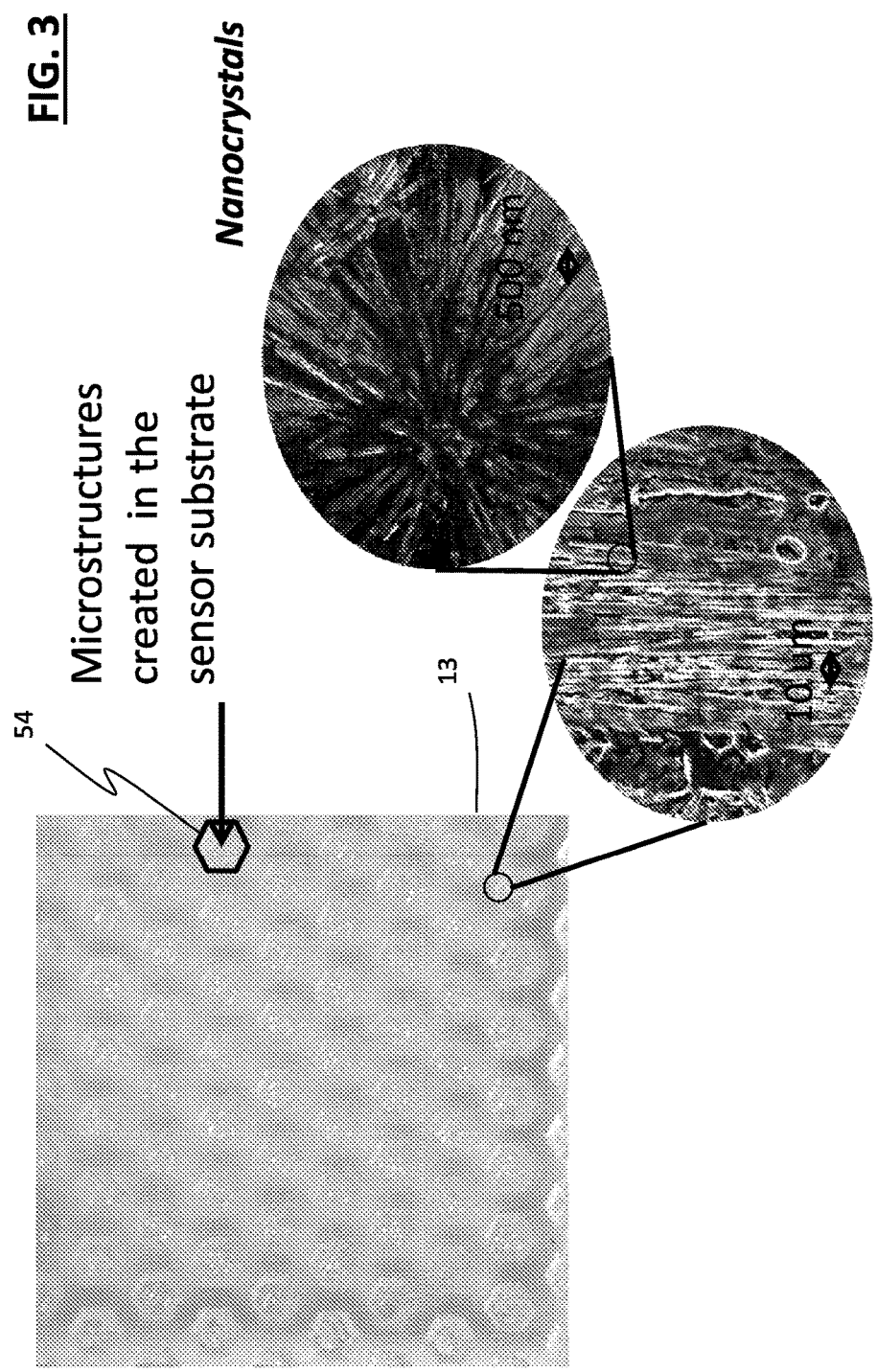

m-cresol purple

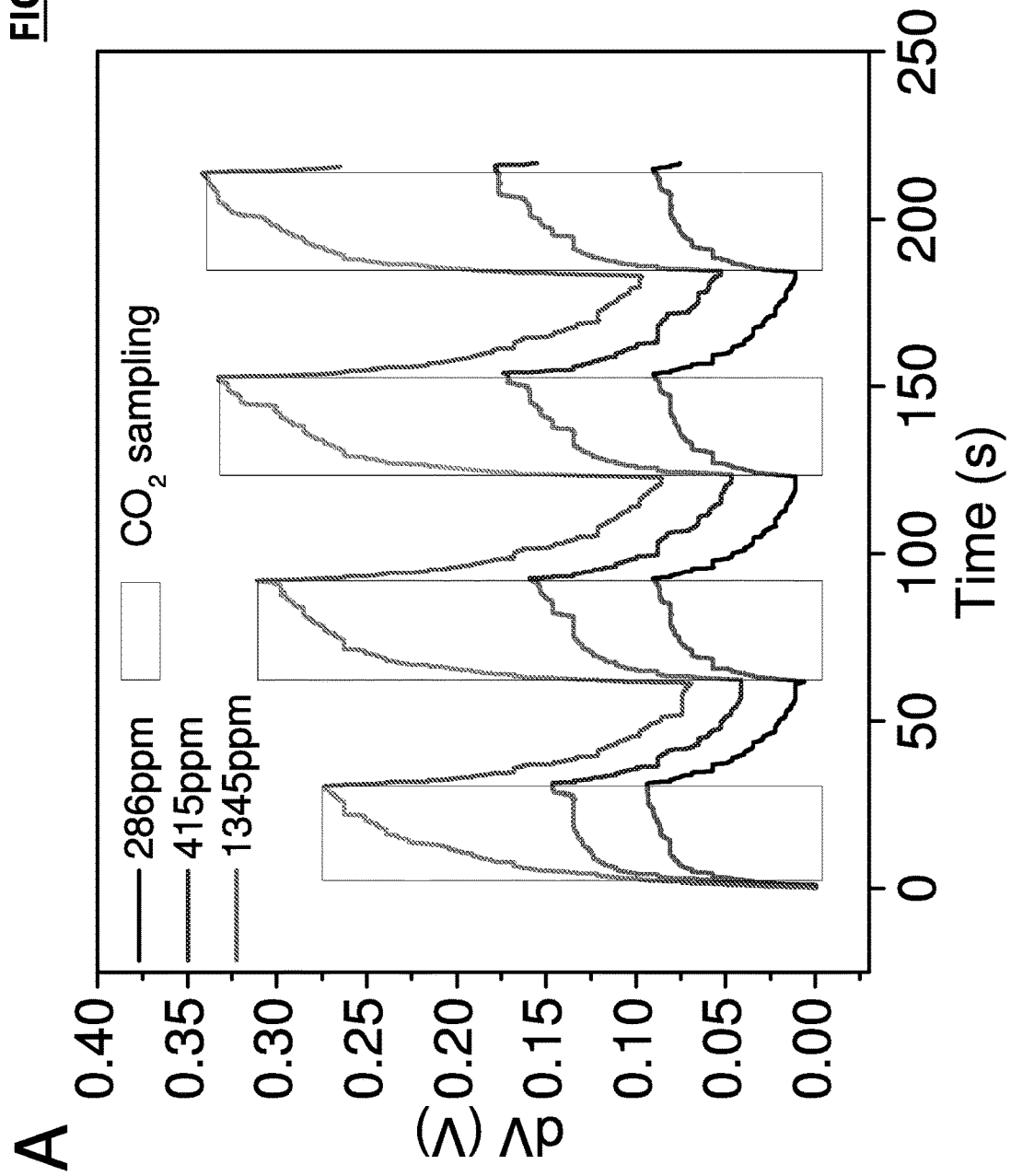

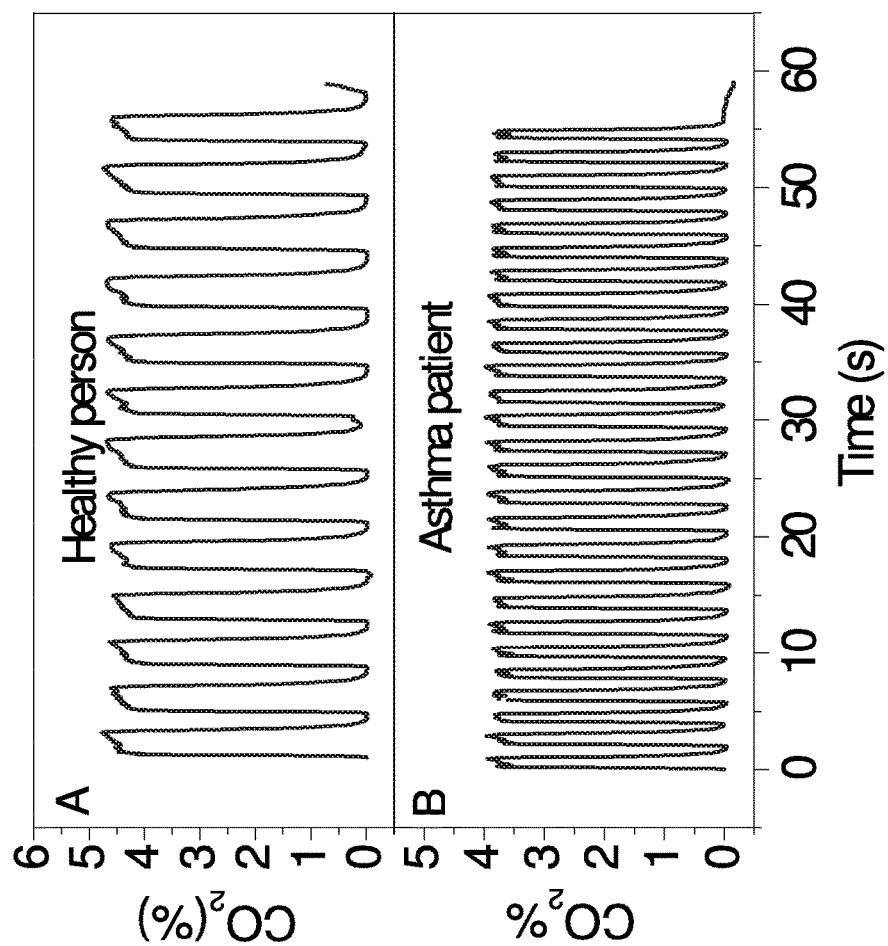

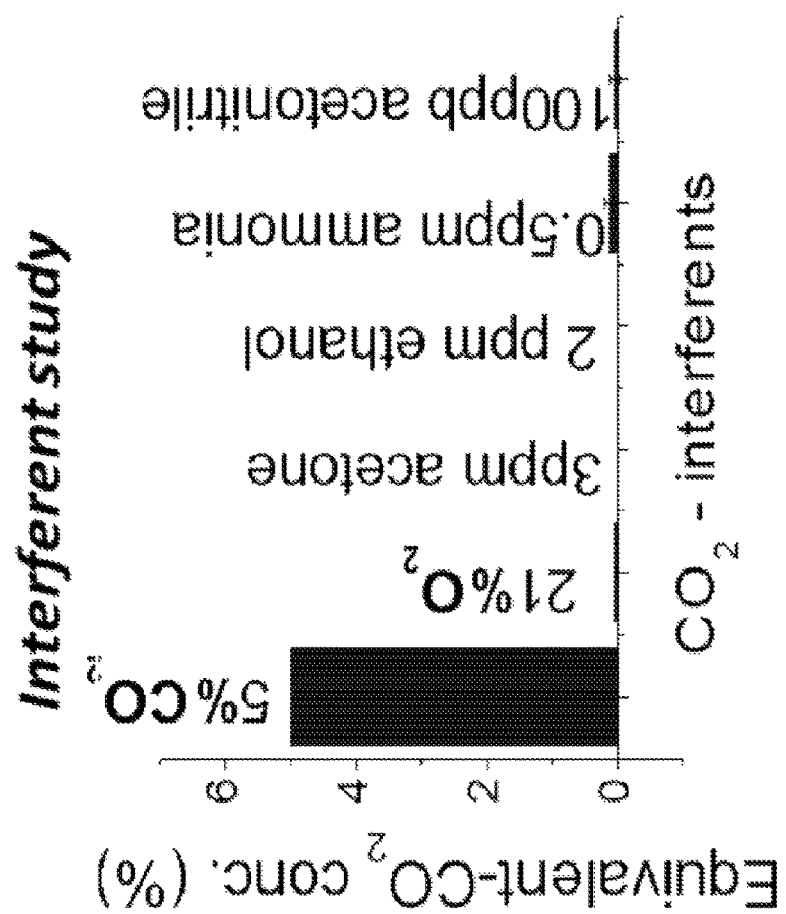

SPECIFIC, REVERSIBLE, AND WIDE-DYNAMIC RANGE SENSOR FOR REAL TIME DETECTION OF CARBON DIOXIDE

STATEMENT REGARDING US FEDERALLY SPONSORED RESEARCH OR DEVELOPMENT

This invention was made with government support under R21 EB014219 awarded by the National Institutes of Health. The government has certain rights in the invention.

TECHNICAL FIELD

The present invention generally relates to carbon dioxide ($CO_2$) detectors, and, more particularly, to a multifunctional carbon dioxide detector for monitoring $CO_2$ concentration in environments including living organisms' breath and the atmosphere.

BACKGROUND

The monitoring of CO2 concentration in both breath and the atmosphere plays an increasingly important role in research, environmental sensing, and personal healthcare [1-19]. The measurement of end-tidal CO2 (EtCO2, the level of carbon dioxide released at the end of expiration) can be used for the evaluation of systemic metabolism, perfusion and ventilation, which provides doctors and patients with a non-invasive and simple method to predict the presence and severity of asthma, Chronic Obstructive Pulmonary Disease (COPD), diabetic ketoacidosis, and a way to evaluate the effectiveness of treatment [8-12, 16-19]. Furthermore, the monitoring of CO2 level in the atmosphere is important for indoor air quality (IAQ) control as the indoor CO2 level is associated with increased prevalence of certain mucous membrane and lower respiratory sick building syndrome (SBS) symptoms [13-15].

Currently, most of the $CO_2$ sensors in the market are based on infrared techniques [20, 21]. Such equipment is either costly and/or suffers from several drawbacks. For example, such devices are adversely affected by strong interference from humidity or require special pretreatment of the gas samples to reduce the humidity level, which limit their applications only in hospitals or in environments with controlled humidity levels. Thus, there is a need in the development of a small, low-cost, and easy-to-use $CO_2$ sensor that anyone can use anytime and anywhere for a more complete and accurate assessment of a patient's disease status at home or, alternatively, in applications that allow better control of the indoor air quality.

The present disclosure provides a new and novel $CO_2$ detector that can be used for the evaluation of respiratory therapy efficiency, prediction of diabetic ketoacidosis and monitoring of indoor air quality. The $CO_2$ detector uses a new ultra-fast and reversible response pH-sensitive nanocomposite material on a microstructured hydrophobic substrate as a sensor element for $CO_2$ detection, which changes color when exposed to $CO_2$; and the concentration of $CO_2$ is determined by measuring the change of light intensity on the sensor element. The $CO_2$ sensor element disclosed herein for the first time has a long shelf life and can be used repeatedly. Also, when interfaced with appropriate hardware, the $CO_2$ detector is capable of synchronizing with mobile devices, such as a cell phone or a tablet, acting as user interfaces so that the users can perform the test anytime and anywhere, and check the real-time data through a specific application.

Colorimetric-based CO2 sensors have been reported in literature [22-28] and also described in patents [29-36] and patent applications [37-41]; however none of the previously reported sensors meet the features of time response, accuracy, specificity, and applicability to real samples as the one described in the present patent application.

U.S. Pat. Nos. 8,449,834; 6,709,403; 5,156,159; 4,994,117; 5,005,572 and 4,943,364 [29-34] disclose examples of $CO_2$ detectors for semi-quantitative determination of $CO_2$ levels in expired air. The $CO_2$ detectors, which change colors in response to the presence of respiratory levels of $CO_2$ (3.5-5%), are mostly used to monitor the placement of endotracheal tube and cannot provide accurate $CO_2$ levels in breath.

U.S. Pat. No. 6,436,347 [35] and U.S. Pat. No. 7,578,971 [36] both describe the use of quaternary ammonium or quaternary phosphonium phase transfer agents with specific molecular structures to produce colorimetric CO2 detectors with fast and reversible response. Although these CO2 detectors may be capable to measure CO2 levels breath-by-breath, their response are not fast enough to monitor the breath CO2 patterns.

US. Patent Applications No. 2013/0259749 [37], and 2013/0150746 by us [41] disclose examples of CO2 detectors for CO2 analysis. While 2013/0259749 [37] emphasizes the configuration of CO2 detector, 2013/0150746 [41] emphasizes the used of the $CO_2$ detector in conjunction with detection on $O_2$. Both applications based their detection on a reactive (sensing) and a control (reference) signal to determine $CO_2$ levels and $O_2$ levels in breath. However, none of the publications emphasizes the importance of a combination of nanocomposite $CO_2$ sensing materials on microstructured hydrophobic surfaces in conjunction with temperature, humidity and flow detection; which actually enables accurate $CO_2$ quantification in, both, breath-by-breath and environment.

BRIEF SUMMARY OF THE DISCLOSURE

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

In one example of the invention, a multifunctional $CO_2$ detector includes a $CO_2$ detection chamber including a gas inlet and a gas outlet. A $CO_2$ sensor is housed in the $CO_2$ detection chamber, where the sensor includes a reversible and selective pH-sensitive nanocomposite sensor element for $CO_2$ detection, and a hydrophobic surface. A flowmeter, thermistor, and a humidity sensor operate to read flow, temperature and compensate for humidity conditions. At least one photodiode is coupled to receive signals from the $CO_2$ sensor and which responds to color change of the sensor element by transducing the color change into a light intensity change. A power source is coupled to power the $CO_2$ detector elements. A microcontroller is electronically coupled to the thermistor, the humidity sensor and the photodiode.

In another aspect, the detector also includes a transmitter and a mobile device coupled to receive data transmitted by the transmitter.

In another aspect, the transmitter includes an antenna for wireless transmission of data.

In another aspect, the mobile device includes a user interface including a display screen.

In another aspect the mobile device includes a computer application residing in the mobile device or accessible thereby to control the user interface and provide the real-time data display, storage, and transmission of data transmitted from the detector.

In another aspect the computer application includes a user profile module, a test module, and a history module, where the modules operate and respond to inputs from the user interface.

In another aspect the test module includes a breath $CO_2$ detection and environmental $CO_2$ detection mode wherein real-time $CO_2$ concentration as a function of time is plotted.

In another aspect the test module includes environmental CO2 detection.

In another aspect the porous hydrophobic surface, which comprises a plurality of microstructures is coated with sensing chemicals. The microstructures provide large surface-to-volume ratio providing dense reactive sites to promote the formation of nano-sized reaction clusters.

In another aspect, the nanocomposite material is hydrophilic pH-sensitive molecular probes.

In another aspect, the nanocomposite material includes pH indicators, such as bromothymol blue, thymol blue, and m-cresol purple, etc.

BRIEF DESCRIPTION OF THE DRAWINGS

While the novel features of the invention are set forth with particularity in the appended claims, the invention, both as to organization and content, will be better understood and appreciated, along with other objects and features thereof, from the following detailed description taken in conjunction with the drawings, in which:

FIG. 1D shows a block diagram of the system components used in one example of a $CO_2$ detection system.

FIG. 2 schematically shows a more detailed example of a sensor used in a pocket-sized multifunctional $CO_2$ detector.

FIG. 3 schematically shows an example of a sensor substrate including microstructures created in the sensor substrate, as well as the connection with the nanocomposite sensing material.

FIG. 7A graphically shows an example application of one embodiment of a $CO_2$ detector to indoor air quality samples demonstrating response of the $CO_2$ sensor exposed to the alternating atmospheres of artificial indoor air samples.

FIG. 9 graphically shows the response of the $CO_2$ sensor exposed to real breath samples from (A) a healthy person and (B) an asthma patient.

FIG. 10 schematically shows an example of study results demonstrating cross-sensitivity of the $CO_2$ sensor to other typical interferent gases present in breath and the atmosphere.

Figures 1A, 1B, 1C:
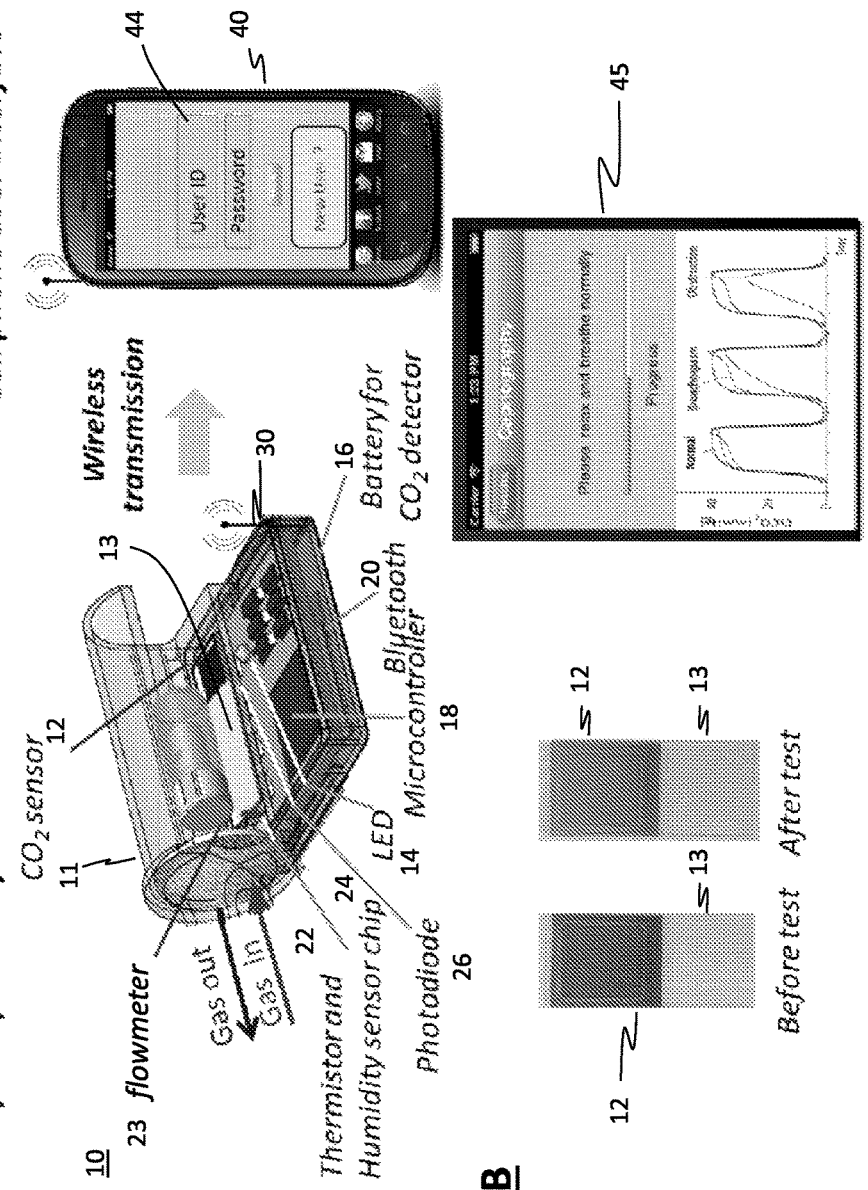
FIG. 1A schematically shows an example of a pocket-sized multifunctional $CO_2$ detector and a user interface on a mobile device (cell phone) for data display, transmission, and storage.
FIG. 1B schematically shows an example of a sensor used in a pocket-sized multifunctional $CO_2$ detector.
FIG. 1C shows an example of a user interface screen display.

In the drawings, identical reference numbers identify similar elements or components. The sizes and relative positions of elements in the drawings are not necessarily drawn to scale. For example, the shapes of various elements and angles are not drawn to scale, and some of these elements are arbitrarily enlarged and positioned to improve drawing legibility. Further, the particular shapes of the elements as drawn, are not intended to convey any information regarding the actual shape of the particular elements, and have been solely selected for ease of recognition in the drawings.

DETAILED DESCRIPTION OF THE PREFERRED EMBODIMENTS

The following disclosure describes several embodiments and systems for multifunctional carbon dioxide ($CO_2$) detector for monitoring $CO_2$ concentration in living organisms' breath and the atmosphere. Several features of methods and systems in accordance with example embodiments are set forth and described in the Figures. It will be appreciated that methods and systems in accordance with other example embodiments can include additional procedures or features different than those shown in the Figures. Example embodiments are described herein with respect to a pocket-sized multifunctional carbon dioxide ($CO_2$) detector. However, it will be understood that these examples are for the purpose of illustrating the principles, and that the invention is not so limited. Additionally, methods and systems in accordance with several example embodiments may not include all of the features shown in the Figures.

Unless the context requires otherwise, throughout the specification and claims which follow, the terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a method or device that "comprises," "has," "includes" or "contains" one or more steps or elements possesses those one or more steps or elements, but is not limited to possessing only those one or more elements. Likewise, a step of a method or an element of a device that "comprises," "has," "includes" or "contains" one or more features possesses those one or more features, but is not limited to possessing only those one or more features. Furthermore, a device or structure that is configured in a certain way is configured in at least that way, but may also be configured in ways that are not listed.

Reference throughout this specification to "one example" or "an example embodiment," "one embodiment," "an embodiment" or combinations and/or variations of these terms means that a particular feature, structure or characteristic described in connection with the embodiment is included in at least one embodiment of the present disclosure. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

DEFINITIONS

Generally, as used herein, the following terms have the following meanings when used within the context of sample collection in fluid environments:

By "concentration" or "concentration of the analyte" as used herein is understood as volume of sample in which a given volume of an analyte is present.

"Contacting" as used herein is understood as bringing two components into sufficient proximity for sufficient time and under appropriate condition of temperature, pressure, pH, diffusion, etc. to allow for the interaction of the two components.

As used herein, "mobile device" has its generally accepted meaning and includes any mobile computer including a tablet, smart phone, complete mobile computer, larger than a mobile phone or personal digital assistant, integrated into a flat touch screen and primarily operated by touching the screen such as, for example, an Apple iPhone® or iPad® tablet computer. These devices can exchange either telephone calls to and from a public telephone network, or/and a wide variety of other services such as text messaging, software applications, MMS, e-mail, Internet access, short-range wireless communications (for example, infrared and Bluetooth).

As used herein, "detecting", "detection" and the like are understood as an assay or method performed for identification of a specific analyte in a sample. The amount of analyte detected in the sample can be none (zero) or below the limit of detection (<LOD), positive and within the calibrated range, or positive and outside of the calibrated range of the assay or method.

"Obtaining" is understood herein as manufacturing, purchasing, or otherwise coming into possession of.

"Operably linked" is understood as a connection, either physical or electronic, between two components of the device, or a component of the device and a remote sensor, data collector, controller, computer, or the like such that the components operate together as desired.

As used herein, "plurality" is understood to mean more than one. For example, a plurality refers to at least two, three, four, five, ten, 25, 50, 75, 100, or more.

As used herein, "real time" is understood as while the process is occurring, for example, collecting data, and preferably transmitting data to a device or person, at the same time the sample is being collected. The data need not be transmitted instantaneously, but may be transmitted within about 1 minute, 2 minutes, 5 minutes, 10 minutes, 15 minutes, or 30 minutes from the time that it was collected, or the collection of the data packet was completed. Data can be sent continuously or periodically in real time for monitoring the progress of a process, or can be sent episodically.

Referring now to FIG. 1A, an example of a pocket-sized multifunctional $CO_2$ detector and a user interface on a mobile device for data display, transmission, and storage is schematically shown. A multifunctional $CO_2$ detector comprises a capnography-spirometry device 10 in communication with a mobile device (cell phone) 40. The device 10 includes a $CO_2$ sensor element 12 on a cartridge 13, a thermistor 22, a humidity sensor chip 24, a photodiode 26, an LED 14, a microcontroller 18, a battery 16 for $CO_2$ detection, and an antenna for wireless transmission 30. In one embodiment, a $CO_2$ detection chamber 11 houses the high performance solid-state optoelectronics components such as the light emitting diode (LED) 14 as light source and at least one photodiode 26 as light detector. The detection chamber 11 also houses the sensor 12 and includes an inlet and an outlet for allowing gas into the sensor area. A thermistor 22, a flowmeter 23 and a humidity sensor 24 operate to read and compensate for humidity conditions (see FIG. 11). The antenna 30 transmits data, preferably by wireless transmission, to the mobile device 40 which includes a user interface 44. The response of the $CO_2$ detector is characterized by measuring the color change of the sensor element 12, which is transduced into a light intensity change on the at least one photodiode 26 of the detection chamber 11. The sensing element 12 can be directly integrated in the detection chamber 11 or integrated into a removable sensor cartridge 13, which in turn, is inserted into the detection chamber. In the latter case, the detection chamber has a sensor cartridge receiver (reservoir).

Referring now to FIG. 1B, one example of a removable $CO_2$ sensor cartridge 13 is shown having different colors before a test and after a test as indicated by color changes.

Referring now to FIG. 1C, an example of a user interface plotting $CO_2$ concentration as a function of time is shown. In operation the test module has two options: breath $CO_2$ detection and environmental $CO_2$ detection. For the breath $CO_2$ analysis, the $CO_2$ concentration as a function of time is plotted, which allows the user to determine how fast and abnormal the breathing cycles are, and how much $CO_2$ is released by the body from circulation to the atmosphere. From the plot, key information, such as arterial blood $CO_2$, body serum bicarbonate and ventilation condition ("normal", "hyperventilation" or "hypoventilation") is displayed. The example display 45 also shows instructions for the user as well as the graphical display showing measured $CO_2$ readings. In addition, a signal processing and feature extraction algorithm is used to identify bronchospasm and obstruction (in COPD) from normal lung function (as best shown in FIG. 5C discussed in more detail herein below).

Referring now to FIG. 1D, a block diagram of system components used in one example of a $CO_2$ detection system is shown. Also, when interfaced with appropriate hardware and software modules as described herein, the $CO_2$ detector is capable of synchronizing with mobile devices acting as user interfaces so that the users can perform the test anytime and anywhere, and check the real-time data through a specific application. The composite contains catalysts and reaction media, which further enhance the reversibility of the reaction kinetics. The catalysts can be quaternary ammonium compounds, such as tetramethylammonium hydroxide, tetraethylammonium hydroxide, n-hexadecyltrimethylammonium hydroxide, mixtures thereof and other suitable phase transfer catalysts. The reaction media can include a variety of pH buffer systems including, for example, carbonate/bicarbonate buffer, Tris buffer, barbital buffer, glycine/NaOH buffer, mixtures thereof and other suitable pH buffers.

The molecular probes have low vapor pressure, which is safe for users and enable sensor shelf life of several months. In one such example, a pocket-sized multifunctional carbon dioxide ($CO_2$) detector 100 syncs with the mobile device (cell phone) 40 and a specific application (app) 102 resides in the mobile device or can be accessed thereby to provide the real-time data display, storage, and transmission of the testing results. The app 102 operates the user interface and may have three basic modules: a user profile module 104, a test module 106, and history module 108. The user profile module 104 and other modules may advantageously comprise software programs residing in a computer memory or the like and are designed according to known software programming techniques. For example, the user profile module 104 may operate to prompt the user to create a personal account (date of birth, gender, etc.). Other information and data modules may be added as preferred for specific applications.

Referring now to FIG. 2, a more detailed example of a sensor used in a pocket-sized multifunctional $CO_2$ detector is schematically shown. The multifunctional $CO_2$ detector uses a colorimetric sensing principle to measure $CO_2$ concentration based on detecting color changes of a sensor element printed on a sensor substrate. It incorporates two key components, a new ultra-fast, reversible, sensitive, and selective pH-sensitive nanocomposite sensor element 12 for detections of $CO_2$, and a porous hydrophobic surface 50 as the sensor element substrate. The hydrophobic surface 50 is coated with sensing chemicals affixed to a sensor cartridge 13. The hydrophobic surface 50, which comprises a plurality of microstructures 54 (as best shown in FIG. 3) is used as the sensor substrate to make the sensor immune from high humidity. The microstructures 54 created in the sensor substrates advantageously act to promote the formation of nano-sized reaction clusters (nanocomposite material) with large surface-to-volume ratio providing dense reactive sites. The nanocomposite material operates as pH-sensitive molecular probes that are hydrophilic. When the sensor is used for breath $CO_2$ analysis, the probes can dissolve quickly upon contact with breath condensation to facilitate fast reaction kinetics. This is in contrast to existing $CO_2$ sensors, where water condensation is a major source of interference. The sensor is prepared by casting suitable volumes of the pH-sensitive nanocomposite solution onto the hydrophobic surface, and drying the solution under controlled ambient conditions that allows the formation on nanocrystalline clusters. In one useful embodiment the hydrophobic sensor substrate may advantageously be polytetrafluoroethylene, polyamide, polyvinylidene fluoride or acrylic based fluorinated polymers.

Figure 4:
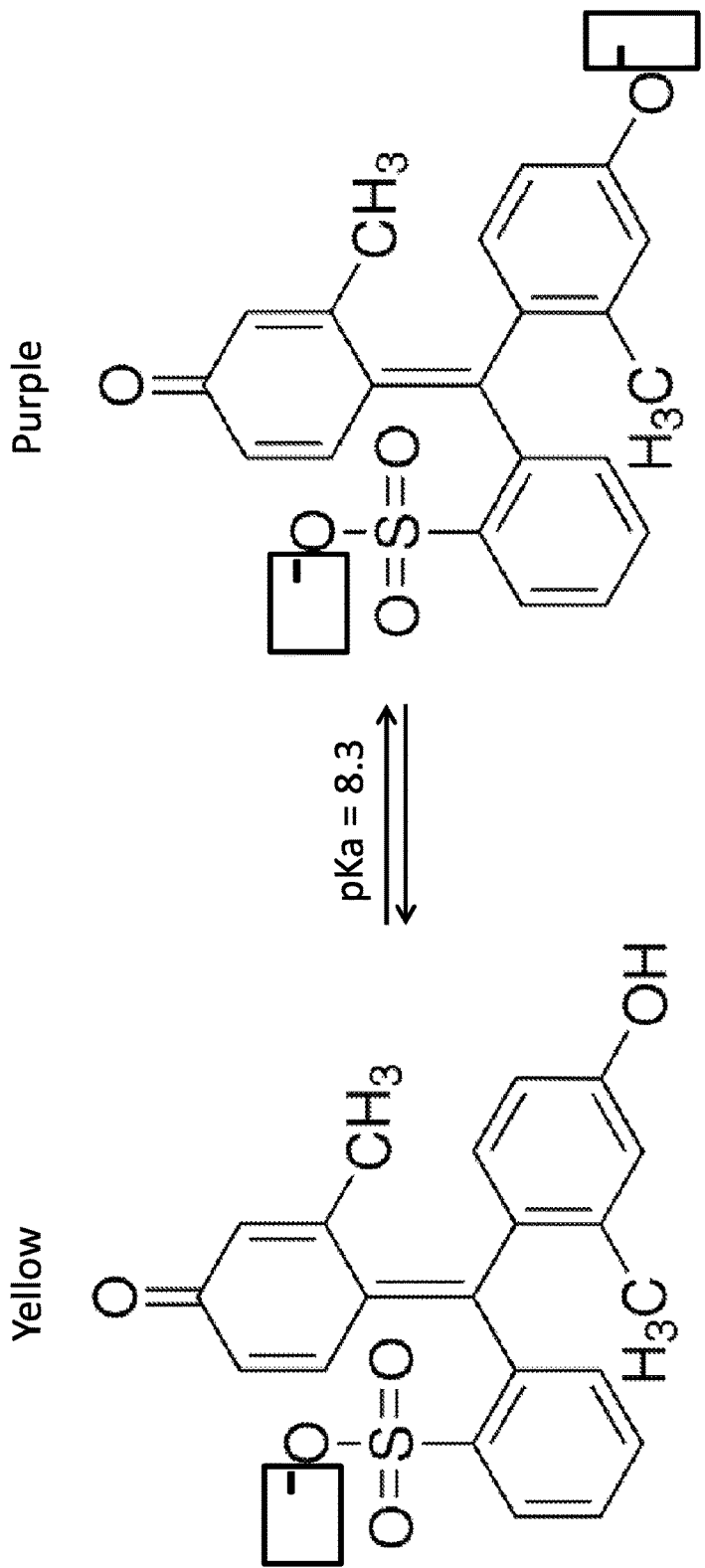
FIG. 4 shows a composite sensing probe used in one example of a $CO_2$ sensor.

Referring now to FIG. 4, the chemical formula for an example of a nanocomposite sensing material used for the CO2 detector is shown. The detector includes a new ultra-fast and reversible response pH-sensitive nanocomposite material as sensor element for CO2 detection, which changes color when exposed to CO2; and the concentration of CO2 is determined by measuring the change of light intensity on the sensor element. The pH-sensitive molecular probe can include a variety of different and suitable materials, such as thymol blue, bromothymol blue, bromocresol purple, litmus, m-cresol purple, cresol red, mixtures thereof and other suitable pH-sensitive dyes.

In one example, the composite material comprises m-cresol purple which reacts as shown in the FIG. 4. m-cresol purple acts as a weak acid in solution. It can thus be in protonated or deprotonated form, appearing yellow or purple respectively. The deprotonation of the neutral form results in a highly conjugated structure, accounting for the difference in color.

Figure 5A:
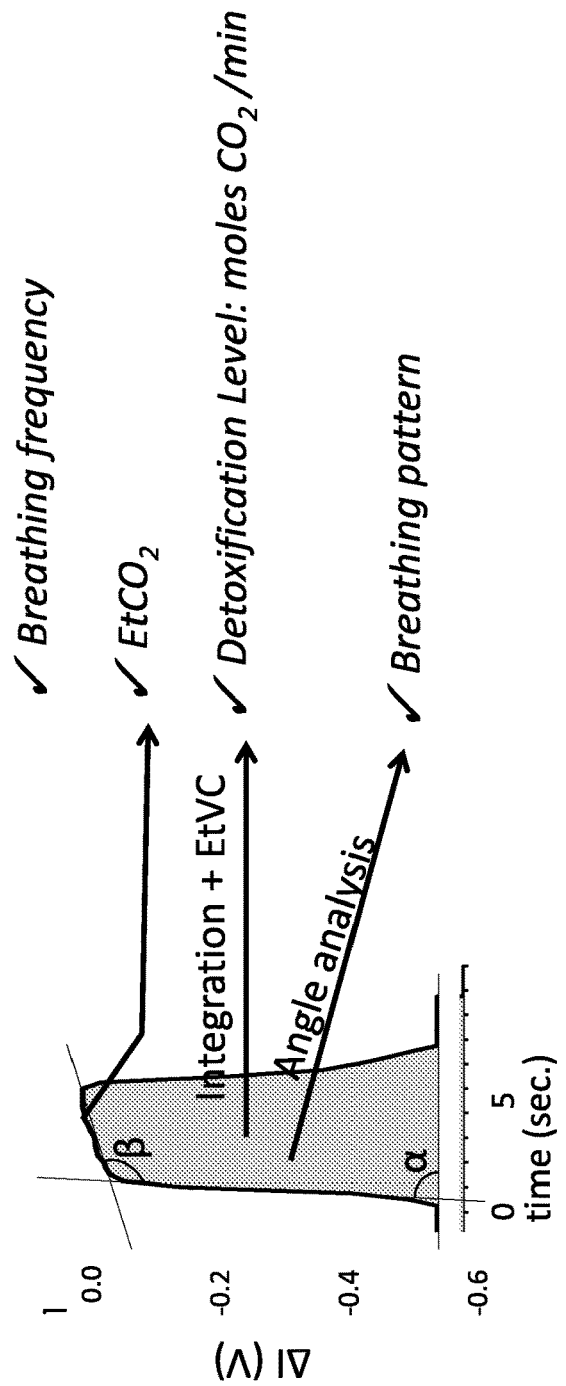
FIG. 5A represents an example of a $CO_2$ profile and related signal processing and feature extraction algorithm for the identification of lung function parameters.

Referring now to FIG. 5A, an example of a $CO_2$ profile and related signal processing and feature extraction algorithm for the identification of lung function parameters is graphically shown. Breathing frequency, end-tidal carbon dioxide ($EtCO_2$), detoxification level (moles of $CO_2$ per min.), and breathing pattern are assessed as follows: 1—Breathing frequency is assessed from the number of breathing cycles (equivalent to $CO_2$ exhalation cycles) performed in one minute; 2—$EtCO_2$ is determined from the maximum $CO_2$ concentration recorded at the end of a single exhalation cycle; 3—Detoxification level is assessed from the integration of the signal of $CO_2$ levels as a function of time during a single exhalation cycle; and 4—breathing pattern is assessed from analysis of changes of $CO_2$ levels during exhalation stages (take-off state, $\alpha$; and alveolar plateau, $\beta$, angles) of a single breath cycle.

Figure 5B:
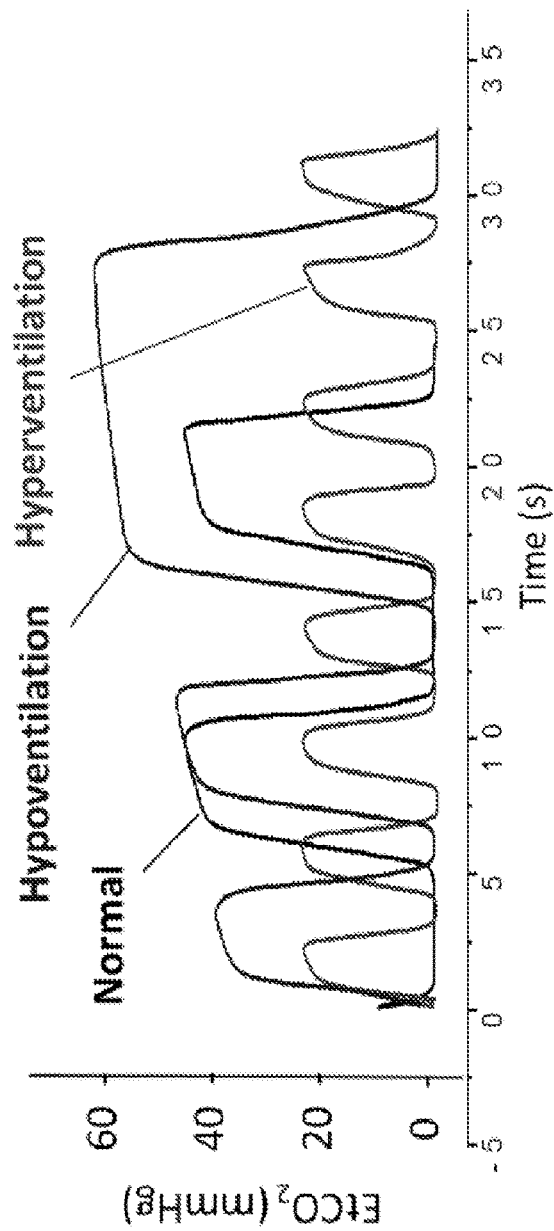
FIG. 5B graphically shows an example application of one embodiment of a $CO_2$ detector to $CO_2$ breath samples coming from patients with normal, low (hypoventilation), and high (hyperventilation) breathing frequency.
Figure 5C:
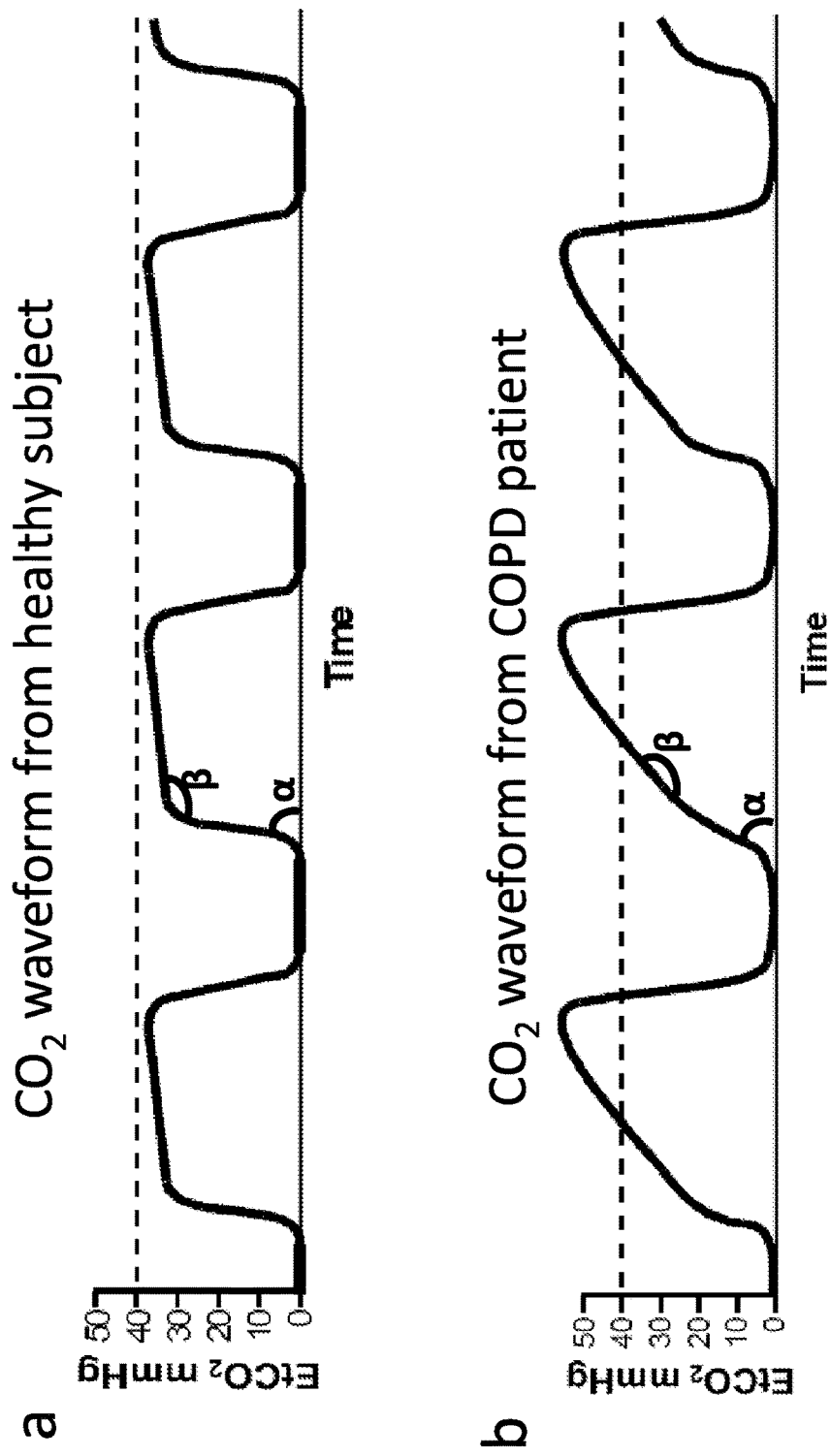
FIG. 5C graphically shows an example application of one embodiment of a $CO_2$ detector to $CO_2$ breath samples coming from: (a) a healthy person, and (b) a patient with COPD.

In general, the normal range of $EtCO_2$ level is between 35-45 mmHg. An elevated $EtCO_2$ level (higher than 45 mmHg) and decreased respiratory frequency (<6 breaths/min) are typically indications of hypoventilation, which may be caused by fever, sepsis, pain, severe difficulty breathing, depressed respirations, chronic hypercapnia and altered mental status such as overdose, sedation and intoxication. In contrast, a reduced $EtCO_2$ level (lower than 35 mmHg) and increased respiratory frequency (>20 breaths/min) may be the indications of hyperventilation, which may relate to anxiety, bronchospasm, pulmonary embolus and cardiac arrest (See FIG. 5B).

For the patients with COPD or asthma, their $CO_2$ profiles exhibit a characteristic "shark fin" shape that differs from that of subjects with normal lung function. As shown in FIG. 5C (b) for COPD patient, the take-off angle ($\alpha$) of the expiratory upstroke phase is decreased and the alveolar plateau elevation angle ($\beta$) is increased in $CO_2$ profiles.

Figure 6A:
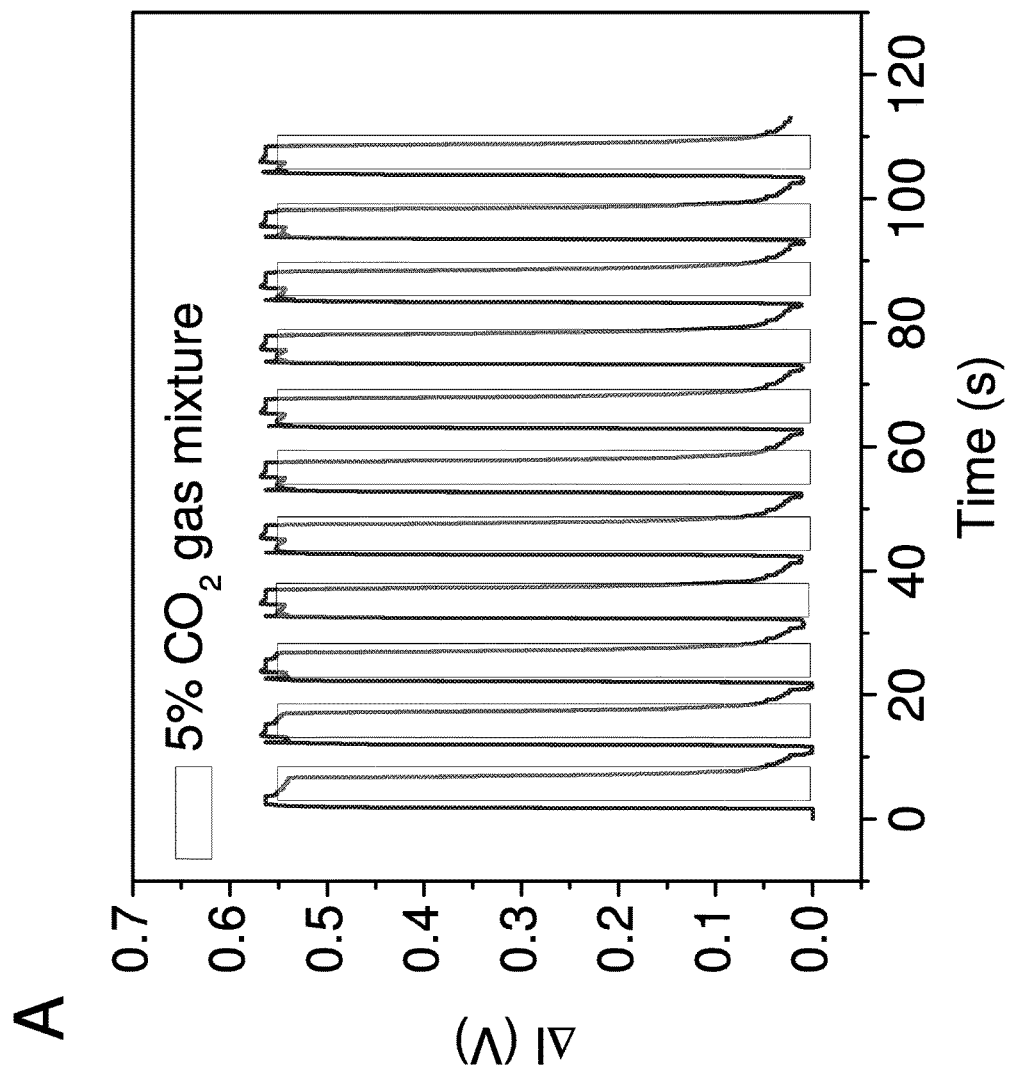
FIG. 6A graphically shows an example application of one embodiment of a $CO_2$ detector to $CO_2$ breath samples demonstrating response of the ultra-fast and reversible $CO_2$ sensor exposed to the alternating atmospheres of ambient air and artificial breath sample containing 5% $CO_2$.

Referring now to FIG. 6A, an example of the application of a $CO_2$ detector to $CO_2$ breath samples demonstrates response of the ultra-fast and reversible $CO_2$ sensor exposed to the alternating atmospheres of ambient air and artificial breath sample containing 5% $CO_2$ is shown. The light intensity immediately increased as $CO_2$ interacted with the sensing system and reduced as ambient air passed through the device. The $CO_2$ detector disclosed herein is capable of performing both breath $CO_2$ analysis and environmental $CO_2$ analysis (as shown below with respect to FIG. 7A-7B).

For the breath $CO_2$ analysis, the $CO_2$ detector analyzes real time $CO_2$ concentration profiles, the end-tidal $CO_2$ (EtCO$_2$, the level of carbon dioxide released at the end of expiration), and the total $CO_2$ release per unit time for evaluation of systemic metabolism, perfusion and ventilation (as best shown in FIG. 5).

Figure 6B:
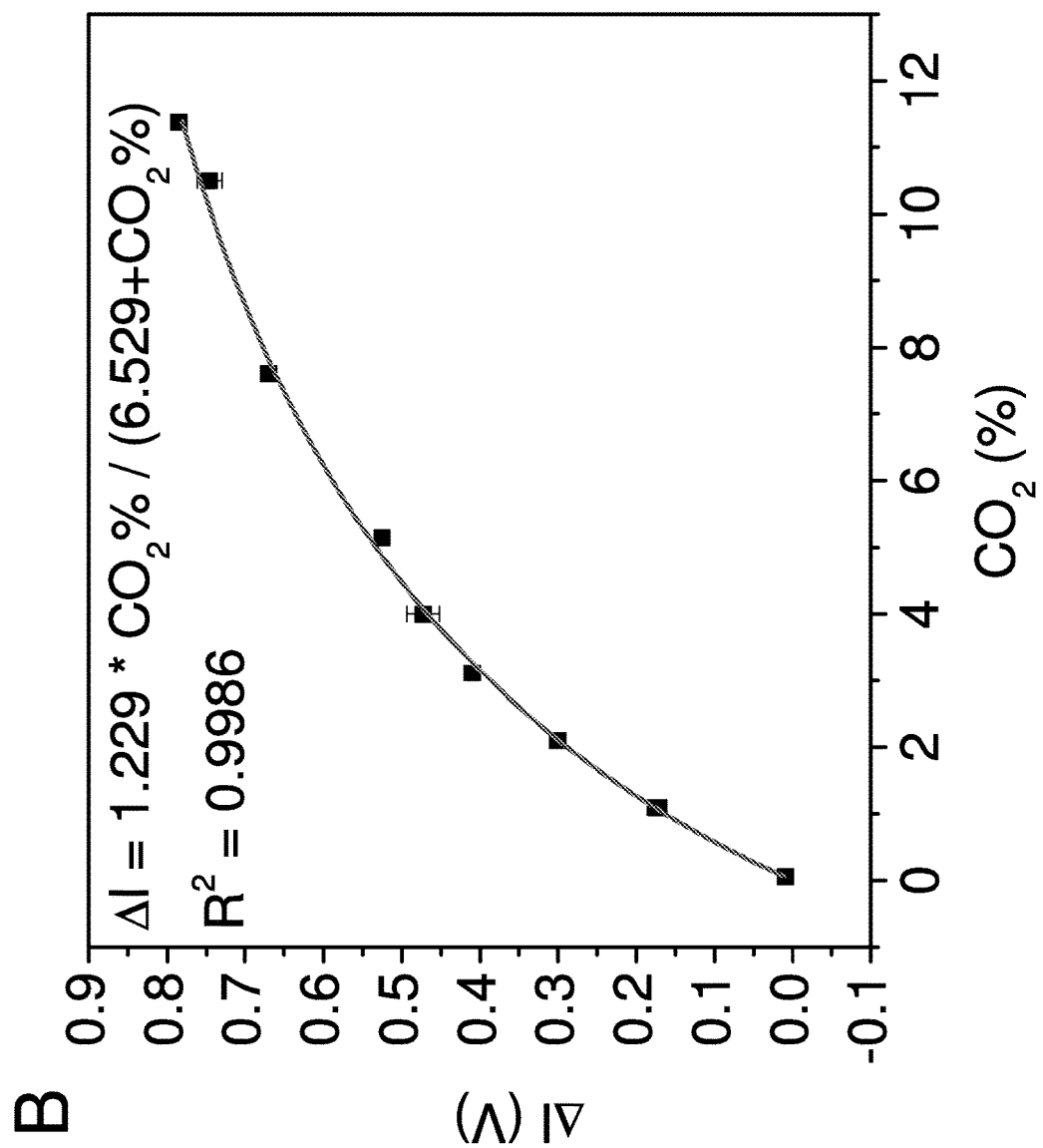
FIG. 6B graphically shows an example application of one embodiment of a $CO_2$ detector to $CO_2$ breath samples demonstrating maximum change of light intensity of $CO_2$ sensor as a function of the $CO_2$ concentration in artificial breath samples, and the corresponding calibration.

Referring now to FIG. 6B, an example application of one embodiment of a $CO_2$ detector to $CO_2$ breath samples demonstrating maximum change of light intensity of $CO_2$ sensor as a function of the $CO_2$ concentration in artificial breath samples, and the corresponding calibration is shown. Here the light intensity is represented on the Y-axis as $\Delta I$ (V) and the percent concentration of $CO_2$ on the X-axis. Note that $\Delta I$ (V) increases with increased $CO_2$% concentration. For the environmental $CO_2$ analysis, the $CO_2$ level in the atmosphere as a function of time is recorded and displayed, which allows the user for a real-time monitoring of the indoor air quality. The intensity change increased with the increasing concentration of $CO_2$ in the gas samples.

In one application a history module establishes a database for each user, including all the measured data and dates of measurements. The data is stored in the mobile device with an option for the user to authorize data transmission to healthcare professionals via the wireless network, and the information is secured with password protection. It also allows the user or authorized medical professionals to view the historical data via plots and statistical data.

Further Experimental Validation and Characterization of the Sensor:

The response of the $CO_2$ sensor was investigated using the ultrahigh purity air, ambient air, $CO_2$ gas mixtures, and real breath samples. As mentioned above, this sensor can be used for the analysis of $CO_2$ in both human breath and the atmosphere. For breath $CO_2$, initial calibration was performed with $CO_2$ gas mixtures prepared by mixing 80% $N_2$+20% $O_2$ gas with different concentrations of $CO_2$ and then humidified by a thermostatic water bath to simulate the real human breath. The $CO_2$ concentration tested in this system ranged from 0.03% to 11.5%. The ambient air and artificial breath samples were introduced into the $CO_2$ detector alternately at a flow rate of 6 L/min.

Referring now to FIG. 7A, an example of application of a $CO_2$ detector to indoor air quality samples demonstrating response of the $CO_2$ sensor exposed to the alternating atmospheres of ultrahigh purity air and artificial indoor air samples with different $CO_2$ concentrations is shown. Here the X-axis represents time in seconds and the Y-axis represents $CO_2$ ppm proportional to $\Delta I$ (V), where V is a voltage reading. As demonstrated by these results, the $CO_2$ detector disclosed herein can be used for the real-time monitoring of $CO_2$ level in the atmosphere for indoor air quality (IAQ) control. For environmental $CO_2$ analysis, the $CO_2$ gas mixtures simulating indoor air samples were prepared by mixing ultrahigh purity air with $CO_2$ to simulate the indoor air with $CO_2$ concentration ranging from 0 ppm to 1350 ppm. The artificial indoor air samples and ultrahigh purity air were introduced into the $CO_2$ detector alternately at a flow rate of 6 L/min. The light intensity increased as $CO_2$ interacted with the sensing system and reduced gradually as pure air passed through the device.

Figure 7B:
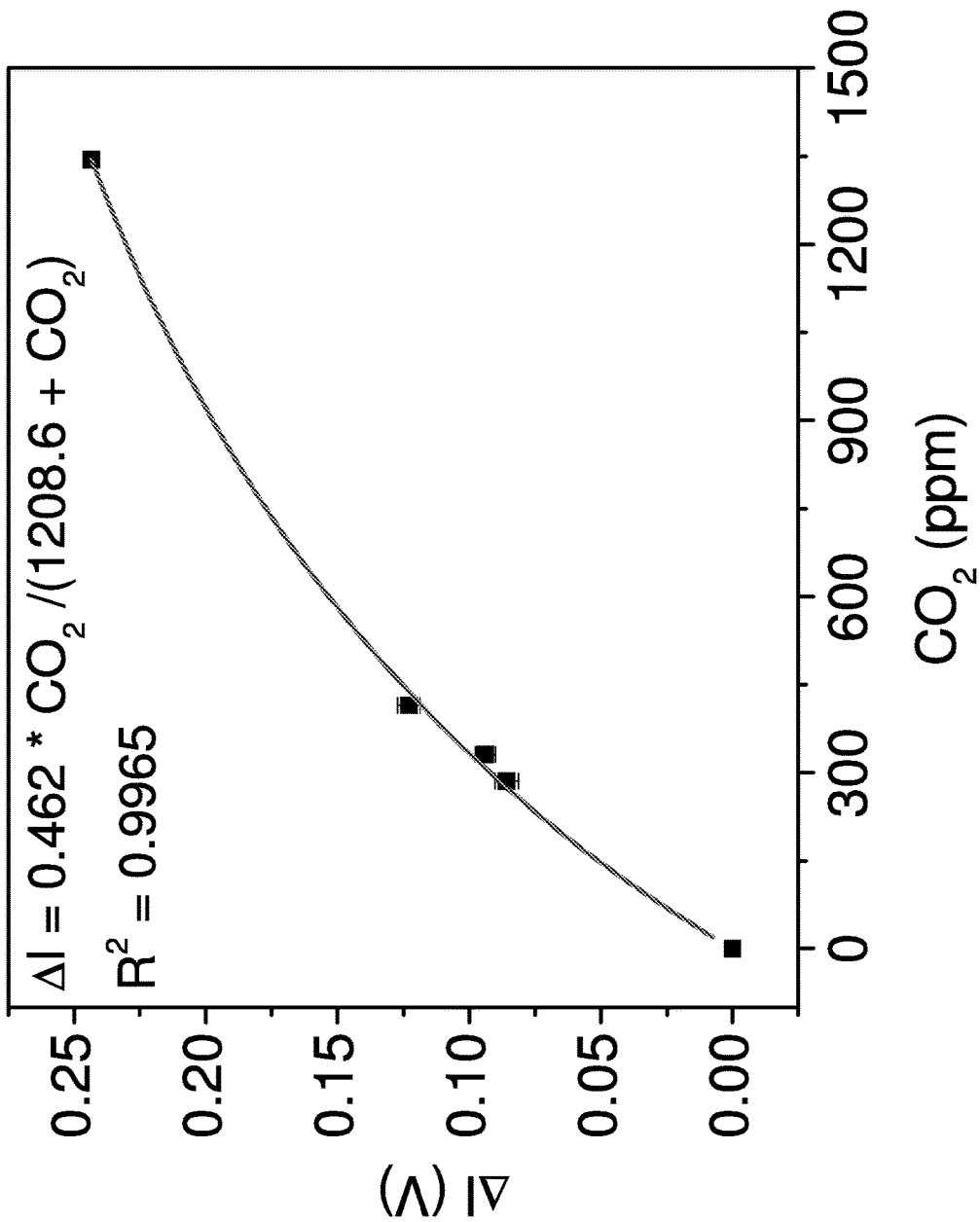
FIG. 7B graphically shows an example application of one embodiment of a $CO_2$ detector to indoor air quality samples demonstrating maximum change of light intensity as a function of $CO_2$ concentration in artificial indoor air samples.

Referring now to FIG. 7B, an example of application of a $CO_2$ detector to indoor air quality samples demonstrating maximum change of light intensity as a function of $CO_2$ concentration in artificial indoor air samples is shown. Here the X-axis represents $CO_2$ ppm and the Y-axis represents light intensity proportional to $\Delta I$ (V), where V is a voltage reading. The intensity change increased exponentially with the increasing concentration of $CO_2$ in the gas samples.

The change of light intensity for the $CO_2$ sensor was used to characterize the color change of the sensor element associated with $CO_2$ concentration: $\Delta I(t)=I(t)-I(0)$ where $I(0)$ is the light intensity prior to the exposure of the sensor surface to breath sample, $I(t)$ is the light intensity at time t during the test. In addition, the stability of the $CO_2$ sensor was also tested using the ambient air and artificial breath samples containing 5% $CO_2$. During the test, the ambient air and artificial breath samples were pumped into the $CO_2$ detector alternately at a flow rate of 6 L/min to simulate the process of respiration. The total time for each test was around 16 min and after each test, the sensor was stored in a small package in the atmosphere until next test. In addition, the performance of this $CO_2$ detector was further validated using real breath samples from volunteers.

Figure 8A:
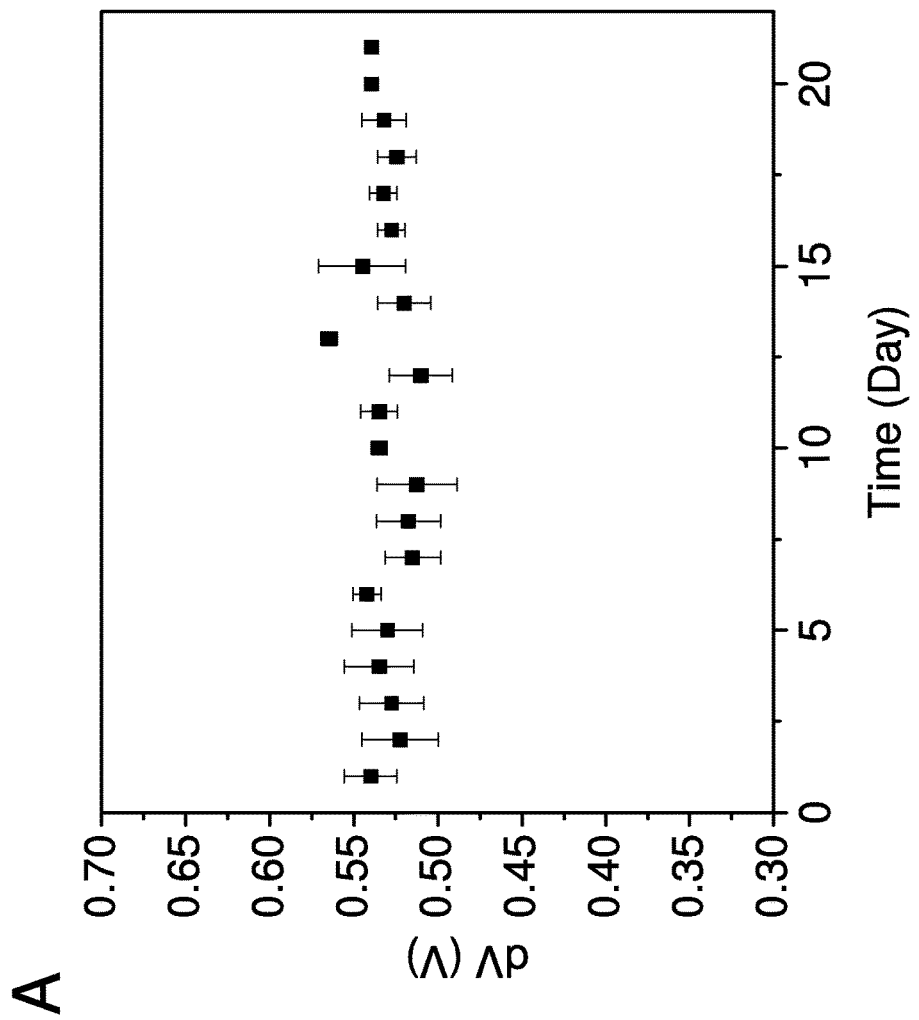
FIG. 8A graphically shows an example of multiple-time use stability (measured as maximum voltage change) of one embodiment of a $CO_2$ sensor.

Referring now to FIG. 8A, an example of multiple-time use stability of the $CO_2$ sensor is shown. The response of a single sensor tested every day for a period of 3 weeks, and showed a total variability of ~10%, which indicated that the sensor can be used multiple times. In this example, every time the sensor was used, breathing cycles were applied for a period of about 16 min. As shown here and in FIG. 8A, the sensor can be used repeatedly and has a long shelf life.

Figure 8B:
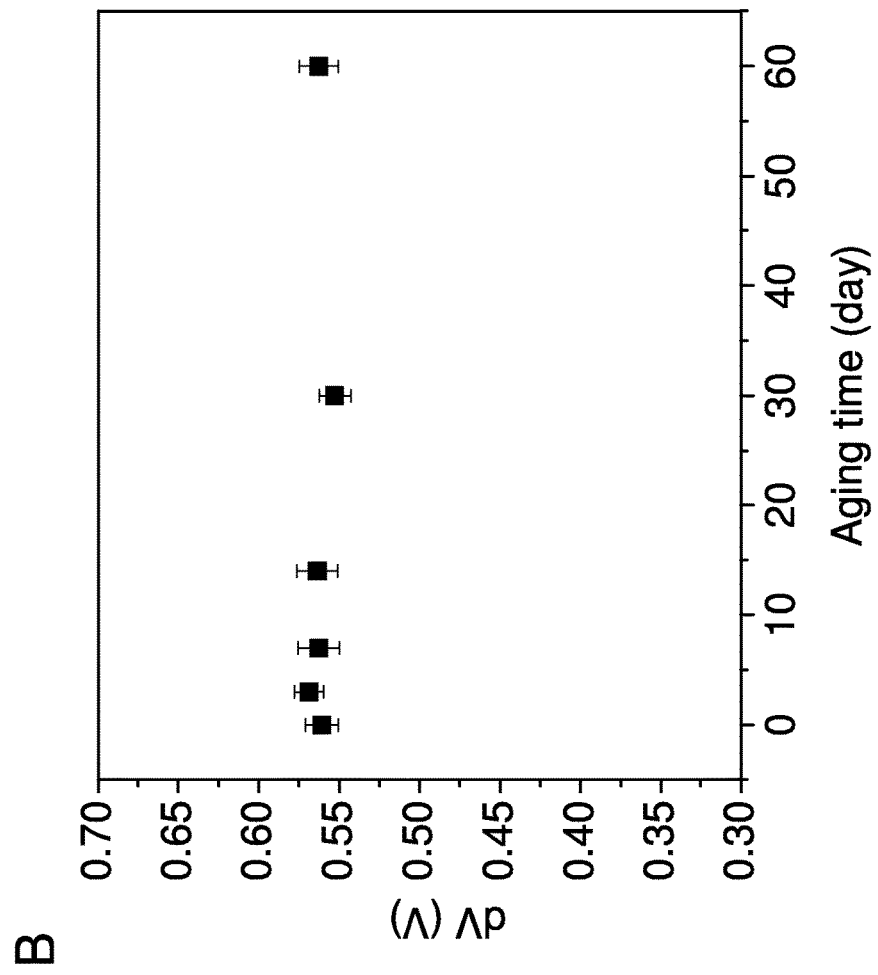
FIG. 8B graphically shows an example of stability (measured as maximum voltage change) of one embodiment of a $CO_2$ sensor with single use as a function of storage time.

Referring now to FIG. 8B an example of stability of the $CO_2$ sensor as a function of storage time is shown. In this example, each test represents a new fresh sensor extracted from a sensor batch prepared and stored at room temperature. For the stability of the sensor as function of storage time, the response of freshly-opened sensors stored at room temperature was evaluated and showed a variability smaller than 10%, which indicated a shelf-life of at least 2 months (tested to the time of this writing) without need of particular refrigeration or storage conditions.

Referring now to FIG. 9, an example of the response of the $CO_2$ sensor exposed to real breath samples from (A) a healthy person and (B) an asthma patient is shown. Features of ultrafast and reversible detection can be observed for real breath samples. $CO_2$ percentage is shown on the abscissa and Time in seconds on the X-axis. For example, in the asthma patient a reversible detection is registered at about 2 second intervals. In contrast, the healthy person registers a reversal at about 4.6 second intervals. The response of the $CO_2$ sensor was reversible and had a fast response to 90% of maximum response. Due to the fast response time, difference in respiration patterns between subjects with different lung capabilities could be clearly observed from the breath-by-breath $CO_2$ waveforms. The analytical performance of the $CO_2$ sensor was compared with a commercial infrared-based detector (not shown). Since the $CO_2$ colorimetric sensor is in direct contact with the breath sample, faster response was observed with respect to the commercial $CO_2$ detector, which relies on mass transport of sample assisted by a pump.

Referring now to FIG. 10, an example of study results demonstrating cross-sensitivity of the $CO_2$ sensor to other typical interferent gases present in breath and the atmosphere is shown. The interference of the other gases typically present in expired or environmental air can be considered to be negligible compared to the response of sensor to 1% of $CO_2$ gas sample, indicating the $CO_2$ is selective. The interferences of other gases in breath and the atmosphere, such as ethanol, acetone, acetonitrile, and $NH_3$ were investigated by introducing the gas mixtures containing pure $N_2$ and the interfering gases into the $CO_2$ detector. The response of $CO_2$ sensor exposed to the interfering gases was compared with the response of sensor exposed to 1% $CO_2$ gas sample.

Figure 11:
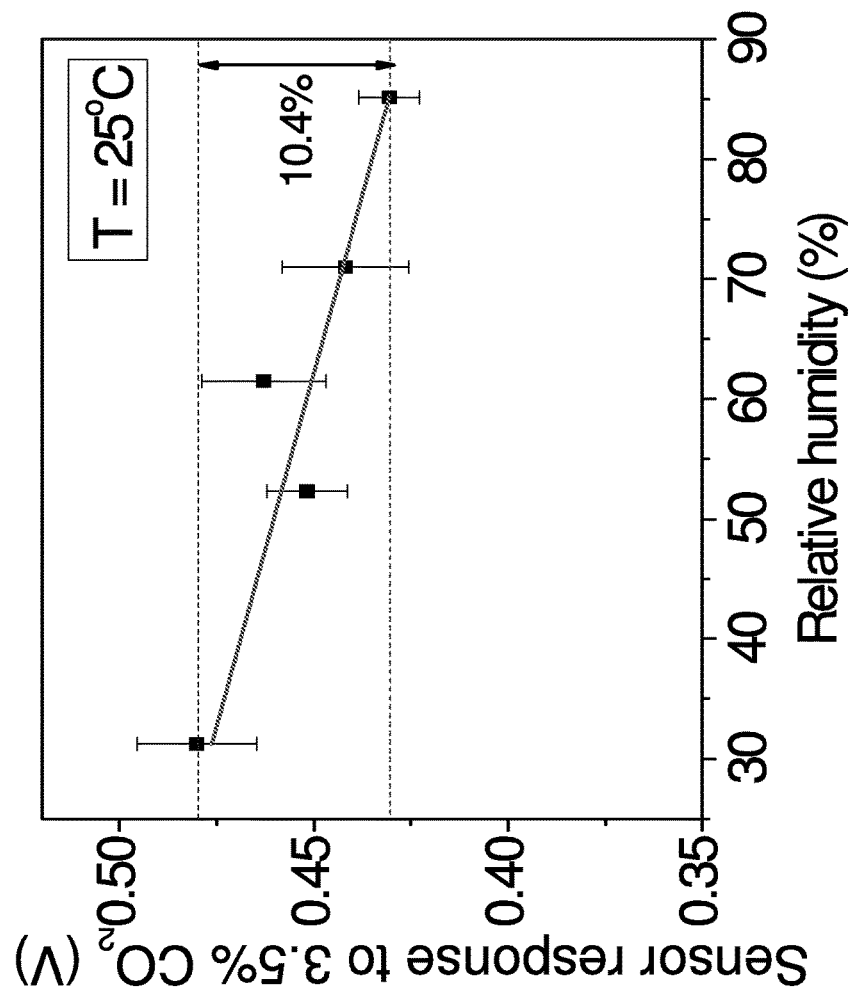
FIG. 11 shows the sensor response to 3.5% $CO_2$ within a range of 30 to 85% of relative humidity.

Referring now to FIG. 11, an example of EtCO$_2$ levels assessed in real breath samples with the CO$_2$ sensor and a commercial infrared-based CO$_2$ analyzer is shown, and demonstrates the high accuracy of the CO$_2$ sensor compared to state-of-the-art CO$_2$ sensing technology.

Figure 12:
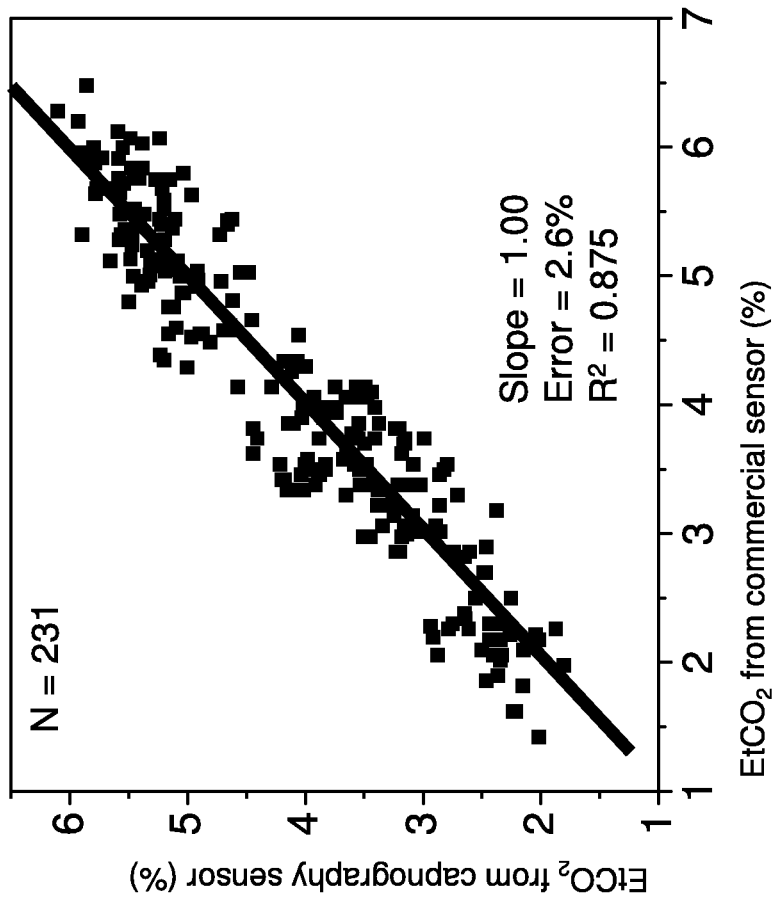
FIG. 12 shows a correlation study of $EtCO_2$ performed with real breath, comparing the results assessed by the $CO_2$ sensor and a commercial $CO_2$ analyzer based on infrared detection.

Referring now to FIG. 12, a correlation study of EtCO$_2$ performed with real breath, comparing the results assessed by the CO$_2$ sensor and a commercial CO$_2$ analyzer based on infrared detection is shown.

The invention has been described herein in considerable detail in order to comply with the Patent Statutes and to provide those skilled in the art with the information needed to apply the novel principles of the present invention, and to construct and use such exemplary and specialized components as are required. However, it is to be understood that the invention may be carried out by different equipment, and devices, and that various modifications, both as to the equipment details and operating procedures, may be accomplished without departing from the true spirit and scope of the present invention.

The following disclosures of the following references are incorporated by this reference in their entirety.

[1] S. Richardson, New trends in capnography, FOCUS: Journal for Respiratory Care & Sleep Medicine, 6(2006).
[2] Chronic Obstructive Pulmonary Disease (COPD), Centers for Disease Control and Prevention Home Page.
[3] N. S. Gooneratne, N. P. Patel, A. Corcoran, Chronic Obstructive Pulmonary Disease Diagnosis and Management in Older Adults, J Am Geriatr Soc, 58(2010) 1153-62.
[4] Asthma cases increase sixfold in 30 years in Japan, Medical News Today, 2004.
[5] Health Central Home Page.
[6] L. J. A. D. M. Mannino, E. S. Ford, S. C. Redd, Chronic Obstructive Pulmonary Disease Surveillance—United States, 1971-2000, Centers for Disease Control and Prevention 2002.
[7] B. S. Kodali, Capnography in 911, Capnography Home Page, 2008.
[8] M. S. Raheem, O. M. Wahba, A nasal catheter for the measurement of end-tidal carbon dioxide in spontaneously breathing patients: a preliminary evaluation, Anesthesia and analgesia, 110(2010) 1039-42.
[9] O. K. Kurt, S. Alpar, T. Sipit, S. F. Guven, H. Erturk, M. K. Demirel, et al., The diagnostic role of capnography in pulmonary embolism, Am J Emerg Med, 28(2010) 460-5.
[10] G. Cacho, J. L. Perez-Calle, A. Barbado, J. L. Lledo, R. Ojea, C. M. Fernandez-Rodriguez, Capnography is superior to pulse oximetry for the detection of respiratory depression during colonoscopy, Rev Esp Enferm Dig, 102(2010) 86-9.
[11] N. H. Ab-Rahman, T. A. Howe, A comparison of capnographic waveform indices and peak flow meter in the monitoring of asthmatic patients in emergency departments, Ann Emerg Med, 51(2008) 476-7.
[12] E. Yanagidate, S. Dohi, Modified nasal cannula for simultaneous oxygen delivery and end-tidal CO2 monitoring during spontaneous breathing, Eur J Anaesth, 23(2006) 257-60.
[13] A. K. Persily, The relationship between indoor air quality and carbon dioxide, Indoor air 19961996, pp. 961-6.
[14] U. Satish, M. J. Mendell, K. Shekhar, T. Hotchi, D. Sullivan, S. Streufert, et al., Is CO2 an Indoor Pollutant? Direct Effects of Low-to-Moderate CO2 Concentrations on Human Decision-Making Performance, Environ Health Persp, 120(2012) 1671-7.
[15] M. G. A. C. A. Erdmann, Indoor carbon dioxide concentrations and sick building syndrome symptoms in the BASE study revisited: Analyses of the 100 building dataset, Indoor Air 20022002, pp. 443-8.
[16] A. T. H. Soleimanpour, M. Niafar, F. Rahmani, S. E. J. Golzari, R. M. Esfanjani, Predictive value of capnography for diagnosis in patients with suspected diabetic ketoacidosis in the emergency department, West J Emerg Med.
[17] Y. Gilhotra, P. Porter, Predicting diabetic ketoacidosis in children by measuring end-tidal CO2 via non-invasive nasal capnography, Journal of paediatrics and child health, 43(2007) 677-80.
[18] E. Garcia, T. J. Abramo, P. Okada, D. D. Guzman, J. S. Reisch, R. A. Wiebe, Capnometry for noninvasive continuous monitoring of metabolic status in pediatric diabetic ketoacidosis, Critical care medicine, 31(2003) 2539-43.
[19] D. M. Fearon, D. W. Steele, End-tidal carbon dioxide predicts the presence and severity of acidosis in children with diabetes, Acad Emerg Med, 9(2002) 1373-8.
[20] B. S. Kodali, Physical Method of CO2 Measurement, Capnography Home Page, 2008.
[21] Capnography, How Equipment Works Home Page.
[22] N. Nakamura, Y. Amao, Optical sensor for carbon dioxide combining colorimetric change of a pH indicator and a reference luminescent dye, Analytical and bioanalytical chemistry, 376(2003) 642-6.
[23] H. Segawa, E. Ohnishi, Y. Arai, K. Yoshida, Sensitivity of fiber-optic carbon dioxide sensors utilizing indicator dye, Sensor Actuat B-Chem, 94(2003) 276-81.
[24] S. M. Borisov, M. C. Waldhier, I. Klimant, O. S. Wolfbeis, Optical carbon dioxide sensors based on silicone-encapsulated room-temperature ionic liquids, Chem Mater, 19(2007) 6187-94.
[25] J. F. Fernandez-Sanchez, R. Cannas, S. Spichiger, R. Steiger, U. E. Spichiger-Keller, Optical CO2-sensing layers for clinical application based on pH-sensitive indicators incorporated into nanoscopic metal-oxide supports, Sensor Actuat B-Chem, 128(2007) 145-53.
[26] M. A. Carvajal, I. M. P. de Vargas-Sansalvador, A. J. Palma, M. D. Fernandez-Ramos, L. F. Capitan-Vallvey, Hand-held optical instrument for CO2 in gas phase based on sensing film coating optoelectronic elements, Sensor Actuat B-Chem, 144(2010) 232-8.
[27] A. Mills, A. Lepre, L. Wild, Breath-by-breath measurement of carbon dioxide using a plastic film optical sensor, Sensor Actuat B-Chem, 39(1997) 419-25.
[28] D. Zhao, D. Miller, D. D. Shao, X. J. Xian, F. Tsow, R. A. Iglesias, et al., A personal device for analyzing carbon dioxide in real time and real breath: Experimental investigation and computational simulation, Sensor Actuat B-Chem, 183(2013) 627-35.
[29] M. Koch, R. C. Murray Jr, Fiber optic CO2 sensor, Spectramed, Inc., US, U.S. Pat. No. 4,943,364, Jul. 24, 1990.
[30] C. G. Fehder, Quantitative carbon dioxide detector, U.S. Pat. No. 4,994,117, Feb. 19, 1991.
[31] D. B. Raemer, D. R. Walt, C. Munkholm, CO2 indicator and the use thereof to evaluate placement of tracheal tubes, Brigham & Women's Hospital, Boston, Mass., US, U.S. Pat. No. 5,005,572, Apr. 9, 1991.
[32] S. Lampotang, J. S. Gravenstein, N. Gravenstein, M. J. Banner, D. Gravenstein, CO2 diagnostic monitor with rupturable container, University of Florida, US, U.S. Pat. No. 5,156,159, Oct. 20, 1992.

[33] J. B. Ratner, Manometer CO2 detector combination, Mercury Enterprises, Inc., Clearwater, Fla., US, U.S. Pat. No. 6,709,403, Mar. 23, 2004.

[34] R. Ostrowski, M. Debreczeny, Carbon Dioxide Detector Having Borosilicate Substrate, Covidien LP, Mansfield, Mass., US, U.S. Pat. No. 8,449,834, May 28, 2013.

[35] A. Cedeon, Indicator Device, Mincor AB, Lidingo (SE), SE, U.S. Pat. No. 6,436,347, Aug. 20, 2002.

[36] J. B. Ratner, D. M. Green, D. W. Crick, M. E. Halpern, Rapid-response reversible dry surface CO2 detector, Mercury Enterprises, Inc., Clearwater, Fla., US, U.S. Pat. No. 7,578,971, Aug. 25, 2009.

[37] E. W. Moretti, R. L. Wood, A. B. Shang, S. S. Yauch, Methods, devices, systems, and compositions for detecting gases, US, US patent application 2013/0259749, Oct. 3, 2013.

[38] B. Cain, J. Cain, F. Johnson, S. Woodard, S. Lee, S. Zhang, Tracheal tube with colorimetric CO2 indicator, US, US patent application 2009/0095290, Apr. 16, 2009.

[39] J. A. Kane, Carbon dioxide (CO2) sensor, US, US patent application 2013/0323845, Dec. 5, 2013.

[40] N. Kobayashi, M. Inoue, H. Dainobu, T. Aoki, K. Sugiyama, I. Takahashi, et al., CO2 sensor and CO2 measuring apparatus, Nihon Kohden Corporation, Tokyo (JP), JP, US patent application 2013/0330161, Dec. 27, 2013.

[41] N. Tao, E. Forzani, Metabolic Analyzer, Arizona Board of Regents for and on behalf of Arizona State University, US, US patent application 2013/0150746, Jun. 13, 2013.

What is claimed is:

1. A pocket-sized multifunctional $CO_2$ detector for use in predicting pulmonary disease comprising:
    a non-invasive CO2 detection chamber including a gas inlet and a gas outlet;
    a $CO_2$ sensor housed in the $CO_2$ detection chamber in direct fluid communication with the gas inlet, where the sensor includes a reversible and selective pH-sensitive nanocomposite sensor element including m-cresol purple, thymol blue, or bromothymol blue for $CO_2$ detection, and a porous hydrophobic surface with microstructures, wherein the porous hydrophobic surface includes a plurality of microstructures made of fluorinated polymers or fluorinated surfaces that have large surface-to-volume ratio providing dense reactive sites to promote the formation of nano-sized reaction clusters;
    a flowmeter;
    a thermistor;
    a humidity sensor;
    at least one light source coupled to receive signals from the $CO_2$ sensor and respond to color changes in the sensor by transducing the color change into a light intensity change;
    at least one photodiode coupled to receive signals from the at least one light source and which responds to light intensity changes by transducing the light intensity changes into electronic signals representing varying degrees of light intensity;
    a power source coupled to power the $CO_2$ detector elements; and
    a microcontroller electronically coupled to the flowmeter, thermistor, the humidity sensor and the photodiode.

2. The detector of claim 1 further comprising:
    a transmitter; and
    a mobile device coupled to receive data transmitted by the transmitter.

3. The detector of claim 2 wherein the transmitter includes an antenna for wireless transmission of data.

4. The detector of claim 2 wherein the mobile device comprises a user interface including a display screen.

5. The detector of claim 2 wherein the mobile device comprises:
    a computer application residing in the mobile device or accessible thereby to control the user interface and provide the real-time data display, storage, and transmission of data transmitted from the detector.

6. The detector of claim 5 wherein the computer application comprises:
    a user profile module;
    a test module; and
    a history module, where the modules operate and respond to inputs from the user interface.

7. The detector of claim 6 where the test module comprises a breath $CO_2$ detection and environmental $CO_2$ detection mode wherein $CO_2$ concentration as a function of time is plotted.

8. The detector of claim 6 where the test module comprises environmental $CO_2$ detection.

9. The detector of claim 1 wherein the porous hydrophobic surface is coated with sensing chemicals affixed to a sensor cartridge.

10. The detector of claim 9 wherein the nano-sized reaction clusters include hydrophilic pH-sensitive molecular probes.

11. The detector of claim 10 wherein the hydrophilic pH-sensitive molecular probes comprise a pH indicator, an amine buffer and phase transfer agents.

* * * * *